US008409297B2

(12) United States Patent
Boone et al.

(10) Patent No.: US 8,409,297 B2
(45) Date of Patent: Apr. 2, 2013

(54) ROBOTIC PROSTHESIS ALIGNMENT DEVICE AND ALIGNMENT SURROGATE DEVICE

(75) Inventors: David Alan Boone, Seattle, WA (US);
Ben Gilbert Macomber, Shoreline, WA (US)

(73) Assignee: Orthocare Innovations LLC, Oklahoma City, OK (US)

( * ) Notice: Subject to any disclaimer, the term of this patent is extended or adjusted under 35 U.S.C. 154(b) by 113 days.

(21) Appl. No.: 12/502,162

(22) Filed: Jul. 13, 2009

(65) Prior Publication Data
US 2010/0161077 A1 Jun. 24, 2010

Related U.S. Application Data

(60) Provisional application No. 61/080,120, filed on Jul. 11, 2008.

(51) Int. Cl.
*A61F 2/48* (2006.01)
*A61F 2/80* (2006.01)

(52) U.S. Cl. .......................................... 623/24; 623/38

(58) Field of Classification Search .................. 606/102; 623/24, 27, 38
See application file for complete search history.

(56) References Cited

U.S. PATENT DOCUMENTS

| | | | |
|---|---|---|---|
| 3,273,168 A * | 9/1966 | Gardner et al. | ................ 623/38 |
| 3,414,908 A * | 12/1968 | Waggott et al. | ................ 623/38 |
| 4,640,138 A | 2/1987 | Meyer | |
| 4,911,023 A | 3/1990 | Izumi | |
| 5,127,420 A | 7/1992 | Horvath | |
| 5,197,488 A | 3/1993 | Kovacevic | |
| 5,360,016 A | 11/1994 | Kovacevic | |
| 5,413,611 A | 5/1995 | Haslam, II | |
| 5,800,565 A | 9/1998 | Biedermann | |
| 5,880,976 A | 3/1999 | DiGioia, III | |
| 5,955,667 A | 9/1999 | Fyfe | |
| 5,995,738 A | 11/1999 | DiGioia, III | |
| 6,301,964 B1 | 10/2001 | Fyfe | |
| 6,513,381 B2 | 2/2003 | Fyfe | |
| 6,761,743 B1 * | 7/2004 | Johnson | .................. 623/38 |
| 6,831,603 B2 | 12/2004 | Menache | |
| 7,150,762 B2 | 12/2006 | Caspers | |
| 7,381,223 B2 | 6/2008 | Kovacevic | |
| 2003/0069644 A1 | 4/2003 | Kovacevic | |

(Continued)

FOREIGN PATENT DOCUMENTS

DE 3701372 A1 7/1988
DE 9408556 U1 7/1994

(Continued)

OTHER PUBLICATIONS

Blumentritt, S., "A New Biomechanical Method for Determination of Static Prosthetic Alignment," Prosthetics and Orthotics International 21(2):107-113, Aug. 1997.

(Continued)

*Primary Examiner* — Bruce E Snow
(74) *Attorney, Agent, or Firm* — Christensen O'Connor Johnson Kindness PLLC

(57) ABSTRACT

A robotic prosthesis alignment device is disclosed that may automatically move the alignment of a prosthesis socket in relation to a prosthesis shank. The robotic prosthesis alignment device provides automatic translation in two axes. The robotic prosthesis alignment device includes angulation mechanics that automatically provide for plantarflexion, dorsiflexion, inversion, and eversion of the foot and shank with respect to the prosthesis socket. A surrogate device is also disclosed that can replicate the alignment achieved with the robotic prosthesis alignment device.

20 Claims, 18 Drawing Sheets

U.S. PATENT DOCUMENTS

| | | | |
|---|---|---|---|
| 2004/0059433 A1 | 3/2004 | Slemker et al. | |
| 2005/0010139 A1 | 1/2005 | Aminian | |
| 2005/0166685 A1 | 8/2005 | Boiten | |
| 2005/0267600 A1* | 12/2005 | Haberman et al. | 623/38 |
| 2006/0022180 A1* | 2/2006 | Selness | 254/104 |
| 2006/0135883 A1 | 6/2006 | Jónsson | |
| 2006/0195197 A1 | 8/2006 | Clausen | |
| 2006/0206214 A1 | 9/2006 | Clausen | |
| 2008/0139970 A1 | 6/2008 | Macomber | |
| 2008/0140221 A1 | 6/2008 | Macomber | |

FOREIGN PATENT DOCUMENTS

| | | |
|---|---|---|
| EP | 0449799 A1 | 10/1991 |
| RU | 2039538 A1 | 7/1995 |
| WO | 9531949 A2 | 11/1995 |
| WO | 0172245 A2 | 10/2001 |
| WO | 2007048374 A1 | 5/2007 |
| WO | 2007048375 A1 | 5/2007 |
| WO | 2007048404 A2 | 5/2007 |
| WO | 2008033852 A2 | 3/2008 |

OTHER PUBLICATIONS

Boone, D., and M. Zhang, "PR 5D7.09—Computerized Prosthesis Alignment Instrument," Proceedings of the 11th World Congress of the International Society for Prosthetics & Orthotics, Aug. 1-6, 2004, Hong Kong, p. 322.

Boone, D., and M. Zhang, "FP 5E4.5—Determination of Prosthetic Malalignment by Fuzzy-Logic Algorithm," Proceedings of the 11th World Congress of the International Society for Prosthetics & Orthotics, Aug. 1-6, 2004, Hong Kong, p. 363.

Chahande, A.I., et al., "Neural Network Models for Customized Alignment of Endoskeleton BK Prosthesis," Neural Networks: IEEE World Congress on Computational Intelligence 6:3507-3511, Orlando, Fla., Jun. 27-Jul. 2, 1994.

Frossard, L., et al., "Development of Preliminary Testing of a Device for the Direct Measurement of Forces and Moments in the Prosthetic Limb of Transfemoral Amputees During Activities of Daily Living," Journal of Prosthetics and Orthotics 15(4):135-142, 2003.

Gusdal, D., et al., "Force Transducer to Assist With Lower Limb Prosthetic Alignment," <http://www.rehab.research.va.gov/prog/99/99prch01.htm> [retrieved Jul. 6, 2009], 2 pages.

Hansen, A., et al., "Automated Alignment System for Prosthetic Feet," Northwestern University Technology Transfer Program, © 2001, <http://www.northwestern.edu/ttp/technology/abstracts/20030.html> [retrieved May 13, 2002], 2 pages.

Jones, D., and J.P. Paul, "Analysis of Variability in Pylon Transducer Signals," Prostethics and Orthotics International 2:161-166, 1978.

Mizrahi, J., et al., "Alignment Procedure for the Optimal Fitting of Lower Limb Prostheses," Journal of Biomedical Engineering 8(3):229-234, Jul. 1986.

Naumann, S., et al., "Dynamic Prosthetic Alignment Assistant," <http://www.rehab.research.va.gov/prog/99/99prch01.htm> [retrieved Jul. 6, 2009], 2 pages.

Nietert, M., et al., "Loads in Hip Disarticulation Prostheses During Normal Daily Use," Prosthetics and Orthotics International 22:199-215, 1998.

Notification of Transmittal of International search Report and the Written Opinion of the International Searching Authority mailed Nov. 4, 2009, in related International Application No. PCT/US2009/050428, filed Jul. 13, 2009.

Parker, K., et al., "Effects of Trans-Tibial Amputee Alignment Changes on Dynamic Socket Loads," Gait and Posture 9(2):135-136, 1999.

Reed, R.D., et al., "Neural Network Aided Prosthetic Alignment," IEEE International Conference on Systems, Man and Cybernetics: Intelligent Systems for the 21st Century, Vancouver, BC, Canada, Oct. 22-25, 1995, pp. 505-508.

Sanders, J.E., et al., "A Measurement Device to Assist Amputee Prosthetic Fitting," Journal of Clinical Engineering 19(1):63-70, Jan./Feb. 1994.

Sanders, J.E., et al., "A Modular Six-Directional Force Sensor for Prosthetic Assessment: A Technical Note," Journal of Rehabilitation Research and Development 34(2):195-202, Apr. 1997.

Sanders, J.E., et al., "A Portable Measurement System for Prosthetic Triaxial Force Transducers," IEEE Transactions on Rehabilitation Engineering 3(4):366-372, Dec. 1995.

Sanders, J.E., et al., "Changes in Interface Pressures and Shear Stresses Over Time on Trans-Tibial Amputee Subjects Ambulating With Prosthetic Limbs: Comparison of Diurnal and Six-Month Differences," Journal of Biomechanics 38:1566-1573, 2005.

Sanders, J.E., et al., "Computer-Aided Prosthetic Alignment for Lower-Limb Amputees," Proceedings of the 15th Annual International Conference of the IEEE Engineering in Medicine and Biology Society, San Diego, Calif., Oct. 28-31, 1993, pp. 1282-1283.

Sanders, J.E., et al., "Dynamic Alignment of a Lower-Limb Prosthesis by Computational Analysis of Gait Force-Time Data," Proceedings, Eighth Biennial Conference, Canadian Society for Biomechanics, Calgary, AB, Canada, Aug. 18-20, 1994, pp. 50-51.

Sanders, J.E., and Daly, C.H., "Measurement of Stresses in Three Orthogonal Directions at the Residual Limb-Prosthetic Socket Interface," IEEE Transactions on Rehabilitation Engineering 1(2):79-85, Jun. 1993.

Seliktar, R., "Computer Aided Dynamic Alignment of Below Knee Prostheses," in J. Raviv (ed.) "Proceedings of the IFIP-IMIA Working Conference on Uses of Computers in Aiding the Disabled: Haifa, Israel, Nov. 3-5, 1981," North Holland Publishing Company, New York, 1982, pp. 87-97.

Winarski, D.J, and J.R. Pearson, "Analytical Description of Minimum Energy Expenditure Surfaces," Journal of Biomechanical Engineering, 110:386-391, Nov. 1988.

* cited by examiner

ROBOTIC PROSTHESIS ALIGNMENT DEVICE AND ALIGNMENT SURROGATE DEVICE

CROSS-REFERENCES TO RELATED APPLICATIONS

This application claims the benefit of U.S. Provisional Application No. 61/080,120, filed on Jul. 11, 2008, incorporated herein expressly by reference for all purposes.

STATEMENT OF GOVERNMENT LICENSE RIGHTS

This invention was made with Government support under Grant Nos. RHD047119 and RHD055709, awarded by the National Institute of Child Health and Human Development. The U.S. Government has certain rights in the invention.

BACKGROUND

Referring to FIG. 1, a conventional prosthesis 10 includes a prosthesis socket 60 into which the amputated limb is placed. The prosthesis socket 60 is connected to a prosthesis shank 30. The prosthesis shank 30 is further connected to a prosthesis foot 20 which bears the weight and makes contact with the ground. The conventional prosthesis 10 includes an adjustable connection, normally between the prosthesis socket 60 and the prosthesis shank 30. For example, the prosthesis shank 30 can have a coupling 40 with an upper end having a concave hemispherical surface. The prosthesis socket can have a pyramid adaptor 50 at the lower end thereof which fits into an aperture provided in the concave surface of the coupling 40. The pyramid adapter 50 includes a surface curved to match the concave surface of the coupling 40. With this configuration, the prosthesis socket 60 can be articulated forward and backward and from side to side with respect to the prosthesis shank 30 and foot 20 to align the prosthesis socket 60 and prosthesis shank 30 to an optimal position that is both efficient and comfortable for the wearer of the prosthesis 10.

A computerized prosthesis alignment system is disclosed in U.S. Application Publication Nos. 2008/0139970 and 2008/0140221, incorporated herein expressly by reference for all purposes. These application publications disclose a torque sensor 104 and control module 106 that provide a means for manually aligning a prosthesis. See FIG. 4 of the publications. The torque sensor 104 is incorporated with a pyramid adaptor (see FIG. 6A of the publications) that then attaches to the lower part of the prosthesis socket 60 and is capable of measuring forces experienced by the prosthesis socket 60. A computer system is then able to analyze the forces and provide feedback to a prosthetist via a graphical user interface, in the form of specific instructions for aligning the prosthesis to an optimum setting. For example, because the alignment of the pyramid adaptor is adjusted using four set screws (elements 117a-d in FIG. 5 of the publications), the computer system can provide instructions, such as the amount of turns required of the set screws to achieve the proper alignment.

The referenced publications further disclose a method of maintaining the alignment once the optimal alignment is achieved. This method relies on the use of a substitute pyramid adaptor that is dimensionally similar to the torque sensor so that it can simply be substituted for the torque sensor. (See element 105 in FIG. 5 of the publications.) The method, however, relies on removing the set screws that hold the alignment according to a specific sequence so as to transfer the substitute pyramid adaptor for the torque sensor without upsetting the previous alignment.

While the above-described computerized prosthesis alignment system is a significant advance in this art, new improvements are continuously being sought that enhance the ways in which a prosthesis can be aligned.

SUMMARY

The disclosure herein provides a robotic prosthesis alignment device that may be coupled to the prosthesis sensor (i.e., transducer) described above that can be controlled by a computer, including, but not limited to, a wireless personal digital assistant (PDA) that enables the prosthetist or wearer to quickly and easily make controlled alignment changes to a prosthesis. Alternatively, software running on a computer can make the changes thus, creating an autonomously self-aligning prosthesis.

A robotic prosthesis alignment device is disclosed in a first embodiment, comprising a translation assembly comprising a first slide deck and a second slide deck that translates in a different direction to the first slide deck; an angulation assembly comprising a first wedge and a second wedge, each wedge being separately capable of rotation; and one or more drivers to move the first and second slide decks and rotate the first and second wedges.

The device of the first embodiment, wherein the translation assembly provides displacement of an object attached to the translation assembly along a two dimensional plane.

The device of the first embodiment, wherein the angulation assembly provides displacement by tilting an object attached to the angulation assembly.

The device of the first embodiment, wherein the movement of the first and second slide decks is linear.

The device of the first embodiment, wherein each wedge comprises a circular member that varies in height around the circumference.

The device of the first embodiment, further comprising, a driver having a revolution counter and, a processor that correlates a translational position to the number of revolutions.

The device of the first embodiment, further comprising, a driver having a revolution counter and, a processor that correlates an angular position to the number of revolutions.

The device of the first embodiment, further comprising, a sensor for each slide deck that measures the position of the slide deck and, a processor that determines the translational position from the sensor measurement.

The device of the first embodiment, further comprising, a sensor for each wedge that measures the position of the wedge and, a processor that determines the angular position from the sensor measurement.

The features disclosed above can be used singly or in combination with any other one or more or all features of the device of the first embodiment.

A prosthesis system is disclosed in a second embodiment, comprising a prosthesis socket for receiving an amputated limb; a prosthesis shank attached to the prosthesis socket; a prosthesis foot attached to the lower end of the prosthesis shank; and a robotic prosthesis alignment device of the first embodiment attached at the joint between the prosthesis socket and the prosthesis shank and/or at the joint between the prosthesis shank and the prosthesis foot, the robotic prosthesis alignment device comprising encoders that provide a translational position and angular position of the prosthesis.

The prosthesis of the second embodiment, wherein the robotic prosthesis device comprises a translation assembly that displaces the prosthesis socket in relation to the prosthesis foot along a two dimensional plane.

The prosthesis of the second embodiment, wherein the robotic prosthesis device comprises an angulation assembly that tilts the prosthesis socket in relation to the prosthesis foot.

The prosthesis of the second embodiment, wherein the robotic prosthesis device comprises, a driver having a revolution counter and, a processor that correlates a translational position to the number of revolutions.

The prosthesis of the second embodiment, wherein the robotic prosthesis device comprises, a driver having a revolution counter and, a processor that correlates an angular position to the number of revolutions.

The prosthesis of the second embodiment, comprising a driver having a revolution counter and a processor that correlates an angular position to the number of revolutions.

The prosthesis of the second embodiment, comprising a sensor that measures the linear position of the translation assembly.

The prosthesis of the second embodiment, comprising a sensor that measures the angular position of the angulation assembly.

The prosthesis of the second embodiment, further comprising a computer in communication with the robotic prosthesis alignment device, wherein the computer computes a gait cycle profile from the translational and angular position.

The prosthesis of the second embodiment, further comprising a memory device having stored therein correlations of linear positions and angular positions to a plurality of gait cycle profiles.

The prosthesis of the second embodiment, further comprising a torque sensor attached to the prosthesis that provides torque measurements to generate a profile of a gait cycle.

The prosthesis of the second embodiment, wherein the computer compares a gait cycle profile generated from translational and angular positions to a gait cycle stored in a database and, computes a translational position and angular position that approximately matches the gait cycle profile stored in the database.

The features disclosed above can be used singly or in combination with any other one or more or all features of the prosthesis of the second embodiment.

A method for automatically controlling the alignment of a prosthesis is disclosed in a third embodiment, comprising measuring a first translational and angular position of a mechanical joint on a prosthesis and providing the measurements to a computer; determining via the computer, a first gait cycle profile from the first translational and angular position of the mechanical joint; obtaining via the computer, a second gait cycle profile stored in a computer memory; comparing via the computer, the first gait cycle profile to the second gait cycle profile and determining differences; calculating via the computer, a second translational position and angular position calculated to reduce the differences between the first and second gait cycle profiles; and moving the mechanical joint to the second translational position and angular position.

The method of the third embodiment, comprising counting the revolutions of a driver to determine the translational position of the mechanical joint.

The method of the third embodiment, comprising counting the revolutions of a driver to determine the angular position of the mechanical joint.

The method of the third embodiment, comprising electronically sensing the translational position and angular position of the mechanical joint.

The method of the third embodiment, wherein the first gait cycle profile is determined by searching a database having stored therein profiles of gait cycles correlating to translational positions and angular positions.

The method of the third embodiment, wherein the first gait cycle profile is determined by torque forces measured along the posterior/anterior plane and right/left planes.

The method of the third embodiment, wherein the mechanical joint attaches a prosthesis socket to a prosthesis shank or a prosthesis shank to a prosthesis foot.

The method of the third embodiment, wherein the mechanical joint comprises a robotic prosthesis alignment device, comprising a translation assembly comprising a first slide deck and a second slide deck that translates in a different direction to the first slide deck; an angulation assembly comprising a first wedge and a second wedge, each wedge being separately capable of rotation; and one or more drivers to move the first and second slide decks and rotate the first and second wedges.

The features disclosed above can be used singly or in combination with any other one or more or all features of the method of the third embodiment.

A surrogate device for transferring an alignment to a prosthesis is disclosed in a fourth embodiment, comprising a first wedge comprising marks, wherein the marks are determinative of a position on the wedge; a second wedge comprising marks, wherein the marks are determinative of a position on the wedge, wherein the first and second wedge are rotationally positionable with respect to each other such that aligning a mark of the first wedge with a mark on the second wedge results in a predetermined angular position.

The surrogate device disclosed in the fourth embodiment, wherein each wedge generally defines a first and a second side tilted at an angle with respect to each, wherein the side of one wedge is positionable on a side of the other wedge, the combined heights of the wedges resulting in an angle of tilting.

The surrogate device disclosed in the fourth embodiment, wherein the first wedge further comprises interlocking projections on the side facing the second wedge, and the second wedge comprises interlocking projections on the side facing the first wedge.

The surrogate device disclosed in the fourth embodiment, further comprising a first deck comprising marks and a second deck comprising marks, wherein the marks are determinative of a position on the decks, wherein the first and second decks are translationally positionable with respect to each other such that aligning a mark of the first deck with a mark on the second deck results in a predetermined translational position.

The features disclosed above can be used singly or in combination with any other one or more or all features of the surrogate device of the fourth embodiment.

A method for maintaining the alignment of a prosthesis is disclosed in a fifth embodiment, comprising setting the angular alignment of a prosthesis, wherein the angular alignment is controlled by a robotic device having first and second wedges that are automatically and rotationally positionable with respect to each other; moving the wedges with respect to each other to achieve an alignment; taking a measurement of the positions of the two wedges in the alignment; assembling a surrogate device having first and second wedges that are assembled to correlate with the measured positions of the wedges of the robotic device to achieve an alignment achieved with the robotic device.

The method of the fifth embodiment, further comprising setting the translational alignment of the prosthesis, wherein the translational alignment is controlled by a robotic device having first, second and third slide decks that are automatically and translationally positionable with respect to each other and taking a measurement of the positions of the slide decks, and assembling the surrogate device having two decks that are assembled to correlate with the measured positions of the slide decks of the robotic device.

The method of the fifth embodiment, wherein the position of the wedges is taken by visually viewing the wedges.

The method of the fifth embodiment, wherein the position of the wedges is taken by an encoder and computer providing the positions.

The method of the fifth embodiment, wherein the position of the slide decks is taken by visually viewing the slide decks.

The method of the fifth embodiment, wherein the position of the slide decks is taken by an encoder and computer providing the positions.

The features disclosed above can be used singly or in combination with any other one or more or all features of the method of the fifth embodiment.

This disclosure provides enabling technology for the difficult implementation of telerehabilitation for patients in areas without adequate professional coverage.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
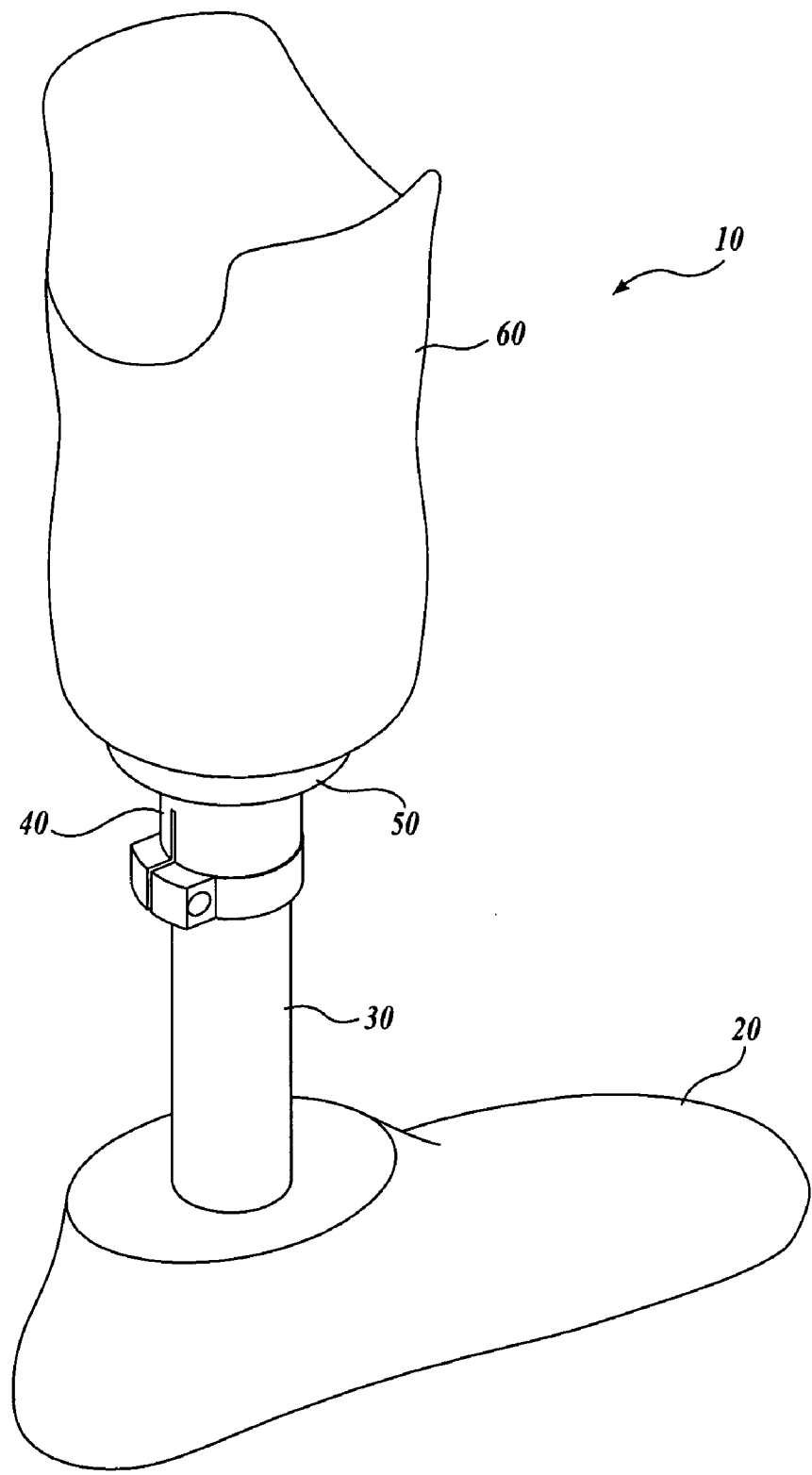
FIG. 1 is a diagrammatical illustration of a prior art prosthesis.
Figure 2:
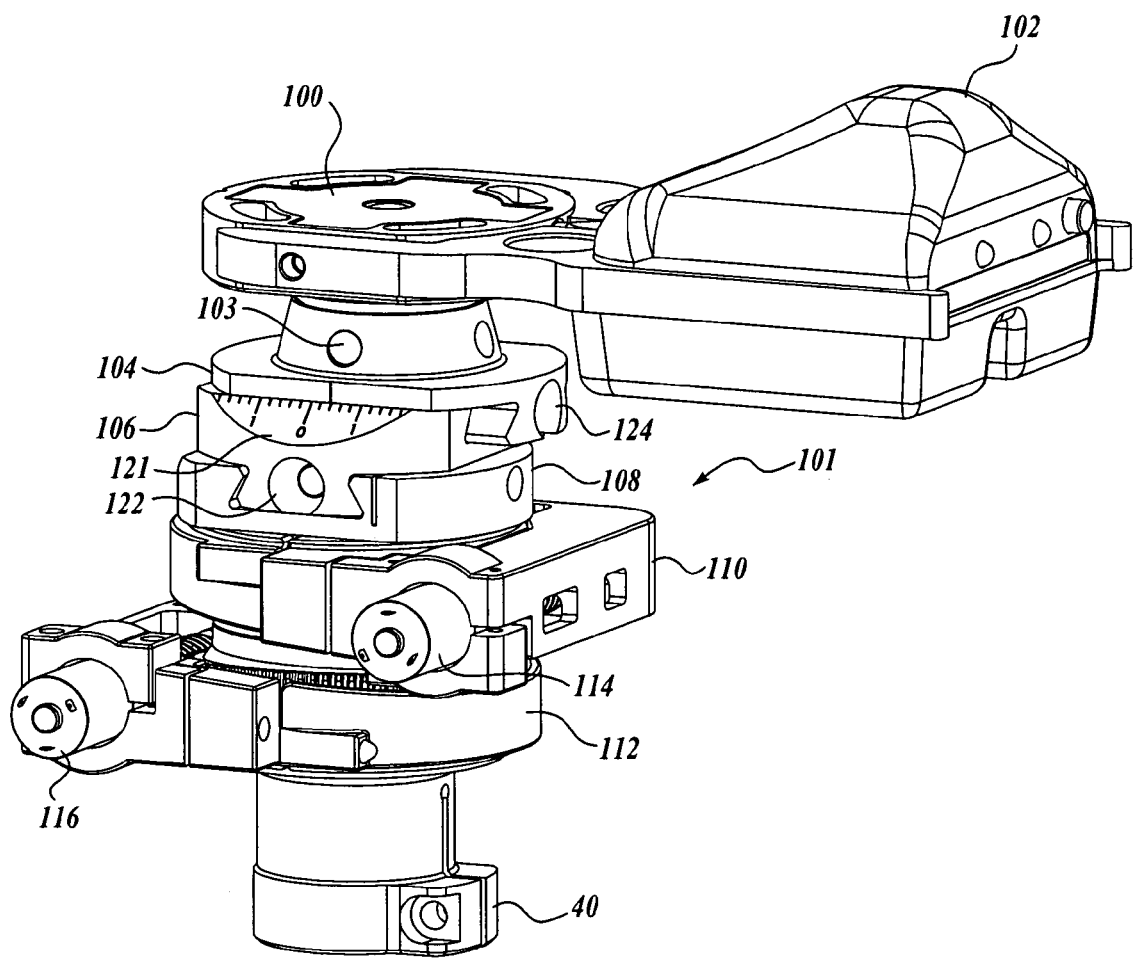
FIG. 2 is a diagrammatical illustration of a robotic prosthesis alignment device coupled to a torque sensor and control module in accordance with one embodiment of the present disclosure.

Referring to FIG. 2, a robotic prosthesis alignment device 101 is disclosed that can be coupled to the torque sensor 100 disclosed in the above-referenced publications to automatically adjust the translational and angular alignment of a prosthesis. However, the robotic prosthesis alignment device 101 can be used without the torque sensor 100. The torque sensor 100 includes an inverted pyramid adaptor that can be coupled to the top of the robotic prosthesis alignment device 101. The pyramid adaptor has a four-sided protuberance that includes four flat sides. Typically, four set screws 103 are used to set the position of the pyramid adaptor and thus align the prosthesis. The base of the pyramid adaptor has a convex surface which rests on a concave surface, thus allowing articulation and adjustment in the left/right plane and the front/back plane. Once the proper alignment is determined, the set screws are tightened against the four-sided protuberance, thus maintaining the alignment. The robotic prosthesis alignment device 101 disclosed herein allows either a user, prosthetist or a computer to take control and automatically perform the alignment. Thus, the set screws 103 may now only be used for a rough alignment and the robotic prosthesis alignment device provides the fine alignment. In one embodiment disclosed herein, the pyramid adaptor can be rigidly mated to the robotic prosthesis alignment device 101. For example, the pyramid adaptor can be attached level to the top surface of the robotic prosthesis alignment device 101. The torque sensor 100 disclosed in the prior publications might be desirable for applications that may require the measurement of torque forces simultaneously with automatic adjustment. For example, the torque sensor 100 used in combination with the robotic prosthesis alignment device 101 can be used to initially obtain a table or database of gait cycle profiles correlating to specific lateral and angular positions. Once the database is created, the robotic prosthesis alignment device 101 can be used without the torque sensor 100. In the latter embodiments, the robotic prosthesis alignment device can be adjusted by referencing a database that correlates a specific lateral and angular position to a gait profile. For example, the database contains profiles of gait cycles correlating to every specific lateral position and angular position that is attainable with the robotic prosthesis alignment device. In another embodiment, a pyramid adaptor and set screws may be omitted from the prosthesis and, all alignment can be made using the robotic prosthesis alignment device 101.

Referring to FIG. 2, the robotic prosthesis alignment device 101 includes a translation assembly and an angulation assembly. Translational movement means movement in two directions which can be orthogonal to each other. Translational movement is movement on a two-dimensional plane. Translational movement can be measured with respect to a reference position, for example, a reference position might be defined as the position when the central axis of the prosthesis shank is concentric with the central axis of the pyramid adaptor at the bottom of the prosthesis socket. Angular movement is movement of an entire plane tilting with respect to a reference plane, such as the ground plane, or the reference plane to which the angle of tilting is referenced might be defined when the central axis of the prosthesis shank is perpendicular to the plane made by the surface of the pyramid adaptor. However, lateral and angular movement can be defined in other ways.

Figure 3:
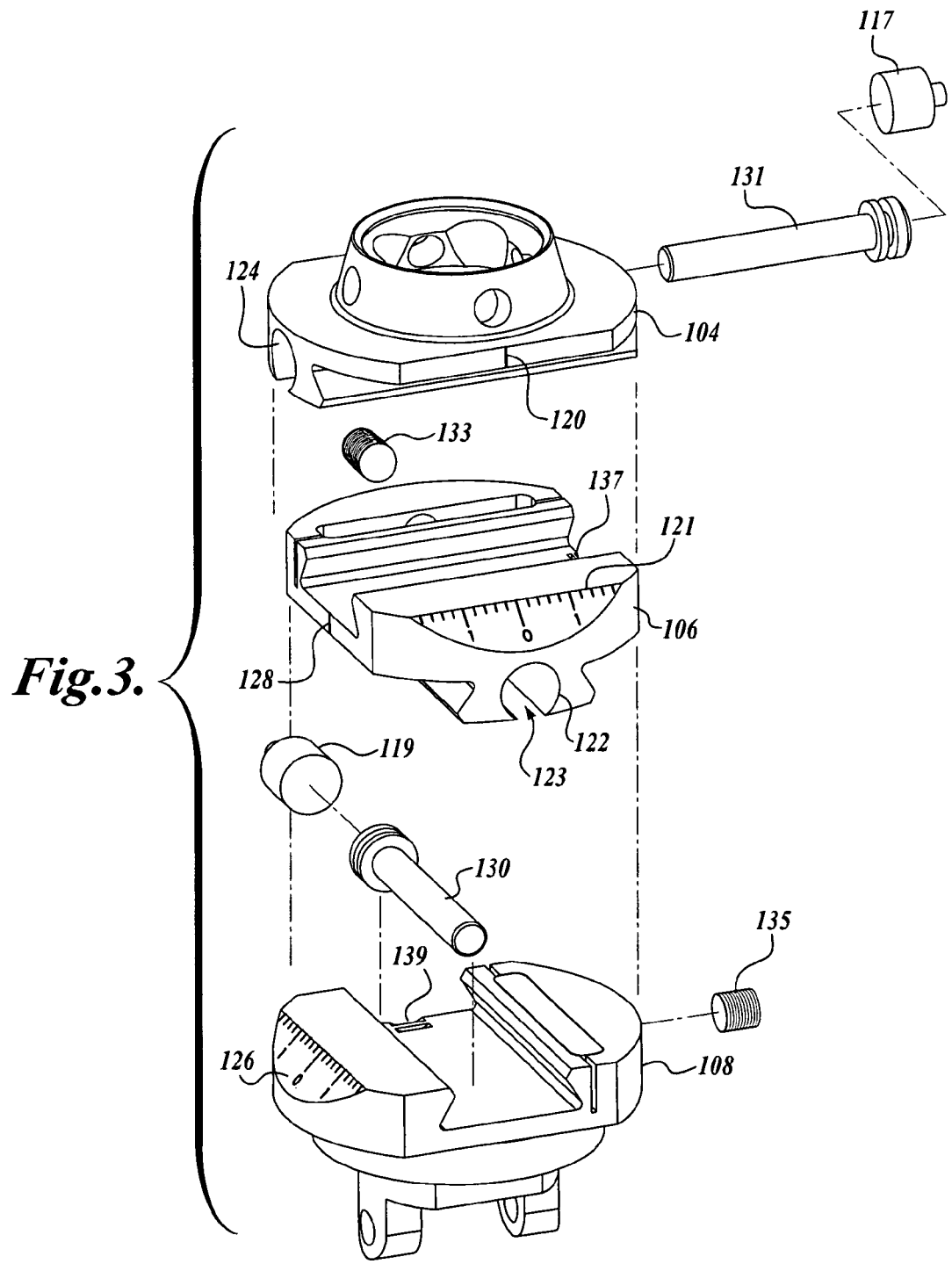
FIG. 3 is a diagrammatical illustration of an exploded view of a portion of the robotic prosthesis alignment device in accordance with one embodiment of the present disclosure.
Figure 4:
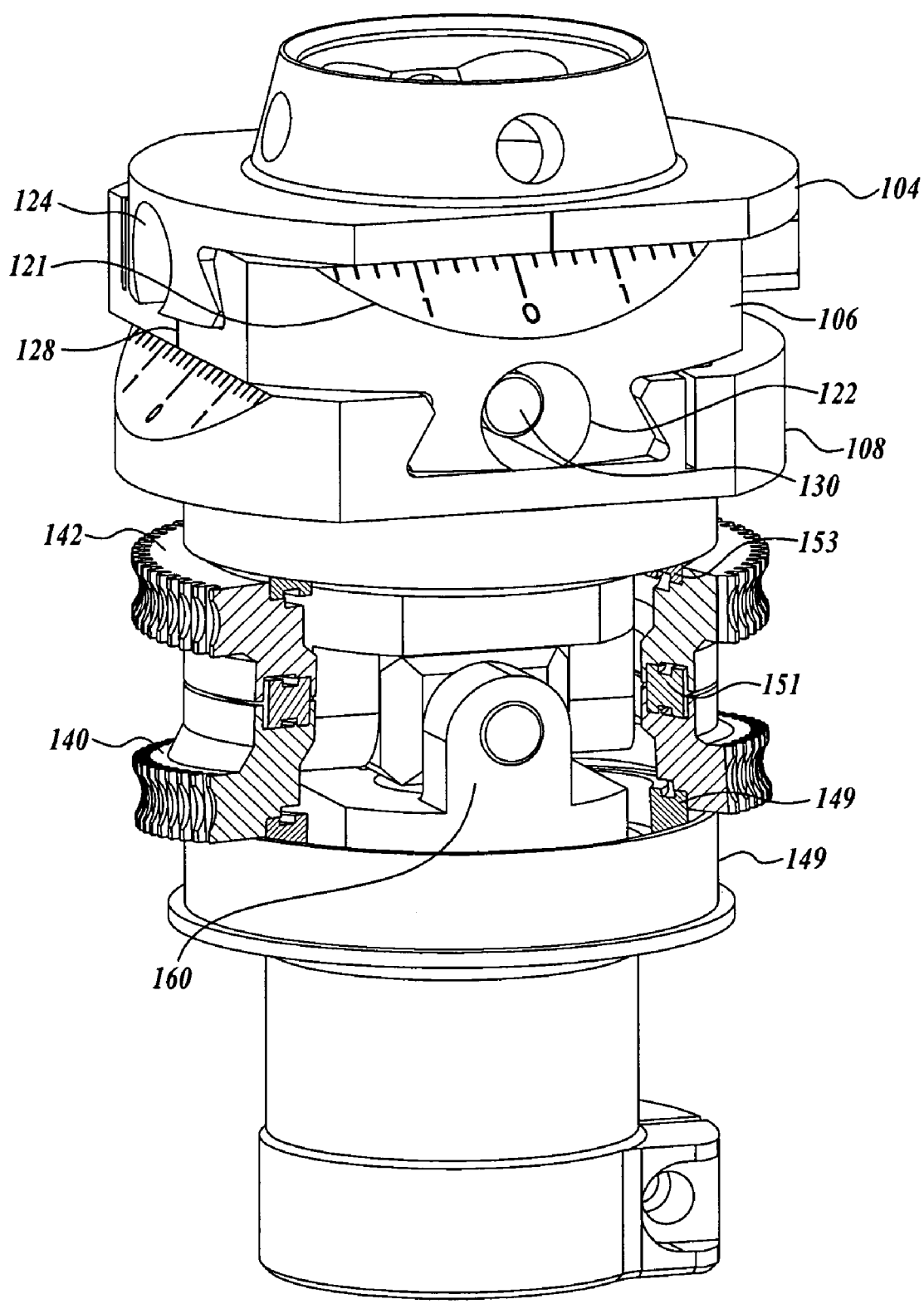
FIG. 4 is a diagrammatical illustration of a cut-away view of a portion of the robotic prosthesis alignment device in accordance with one embodiment of the present disclosure.

The translation assembly comprises robotic slide decks including an upper slide deck 104, a middle slide deck 106, and a lower slide deck 108. Referring to FIGS. 3 and 4, the assembly comprised of the slide decks 104, 106, and 108 is for translation in two axes that are orthogonal to each other. The upper slide deck 104 may include the receptacle or coupling for receiving the pyramid adaptor protuberance that would normally be received by the top of the prosthesis shank. The middle slide deck 106 is positioned below the upper slide deck 104. Slide-locking means are provided at the interface of the upper slide deck 104 and the middle slide deck 106. The slide-locking means can include a pair of interlocking rails, one disposed on the lower surface of the upper slide deck 104 and one disposed on the upper surface of the middle slide deck 106. In one embodiment, the rails may be respectively configured similar to an elongated dovetail "mortise and tenon." The upper slide deck 104 includes a bore 124 within the tenon component extending the length thereof and having an open channel for the entire length at a lower section. A translation screw or worm gear, such as translation screw 131 (FIG. 3) can be used to move slide deck 104 in relation to slide deck 106. The translation screw 131 can be rotated manually. Once the desired translation is achieved, a set screw 133 can be tightened to apply pressure to the side of the translation screw 131 to prevent the translation screw 131 from further rotating. Instead of operating manually, the rotating motion can be provided by an actuator or driver 117 that rotates translation screw 131. In either the manual or driven embodiment, the translation screw 131 is engaged to mating screw slots 137 provided at one end of the mortise component of the middle slide deck 106. The translation screw 131 is then able to engage the slots 137 through the open channel in the bottom of the bore 124. Rotation of the translation screw 131 would then cause the upper slide deck 104 to slide in relation to the middle slide deck 106. In another embodiment, as an alternative to the translation screw, a worm gear, or an Acme screw and nut can be used. In a still further embodiment, the sliding motion could be achieved with a "smart" screwdriver that under wireless command from a PDA, for example, would be used to drive the sliding decks assembly to the desired position, and then could be detached from the assembly. Thus, automation and computer control is possible without the burden of added weight or bulk to the leg. The upper slide deck 104 includes an index mark 120. The middle slide deck 106 includes a graduated scale 121 on a side thereof. The scale can be divided according to any non-dimensional or dimensional units, such as inches or millimeters. Therefore, the amount of travel of the upper slide deck 104 and middle slide deck 106 can be determined by visually noting the location of the index mark 120 on the graduated scale 121 and whether the movement is positive or negative. Alternatively, the relative position of the slide decks 104 and 106 can be determined by a computer and processor. The latter can be achieved by receiving input from the driver 117 and counting the revolutions of the driver that correlate to a certain position. For example, the driver can be driven in one direction to the limit of travel, the counter is initialized to zero and each revolution in the opposite direction can correlate to an increment of travel. Also, switches and sensors, such as magnetic sensors, can be used to measure the position of the slide deck travel.

The lower slide deck 108 is positioned below the middle slide deck 106. Slide-locking means are provided at the interface of the middle slide deck 106 and the lower slide deck 108. The slide-locking means can include a pair of interlocking rails, one disposed on the lower surface of the middle slide deck 106 and one disposed on the upper surface of the lower slide deck 108. In one embodiment, the rails may be respectively configured similar to an elongated dovetail "mortise and tenon." The rails at the interface between the middle slide deck 106 and the lower slide deck 108 are placed perpendicular to the rails at the interface of the middle slide deck 106 and the upper slide deck 104. The middle slide deck 106 includes a bore 122 within the tenon component extending the length thereof and having an open channel 123 for the entire length at a lower section. A translation screw or worm gear, such as translation screw 130 (FIG. 3) can be used to move slide deck 106 in relation to slide deck 108. The translation screw 130 can be rotated manually. Once the desired translation is achieved, a set screw 135 can be tightened to apply pressure to the side of the translation screw 130 to prevent the translation screw from further rotating. Instead of operating manually, the rotating motion can be provided by an actuator or driver 119 that rotates translation screw 130. In either the manual or driven embodiment, the translation screw 130 is engaged to mating screw slots 139 provided at one end of the mortise component of the lower slide deck 108. The translation screw 130 is then able to engage the slots 139 through the open channel 123 in the bottom of the bore 122. Rotation of the translation screw 130 would then cause the middle slide deck 106 to slide in relation to the lower slide deck 108. In another embodiment, as an alternative to the translation screw, a worm gear, or an Acme screw and nut can be used. In a still further embodiment, the sliding motion could be achieved with a "smart" screwdriver that under wireless command from a PDA, for example, would be used to drive the sliding decks assembly to the desired position, and then could be detached from the assembly. Thus, automation and computer control is possible without the burden of added weight or bulk to the leg. The middle slide deck 106 includes an index mark 128. The lower slide deck 108 includes a graduated scale 126 on a side thereof. The scale can be divided according to any non-dimensional or dimensional units, such as inches or millimeters. Therefore, the amount of travel of the middle slide deck 106 and lower slide deck 108 can be determined by visually noting the location of the index mark 128 on the graduated scale 126 and whether the movement is positive or negative. Alternatively, the position of the slide decks 106 and 108 can be determined by a computer and processor. The latter can be achieved by receiving input from the driver 119 and counting the revolutions of the driver that correlate to a certain position. For example, the driver can be driven in one direction to the limit of travel, the counter is initialized to zero and each revolution in the opposite direction can correlate to an increment of travel. Also, switches and sensors, such as magnetic sensors, can be used to measure the position of the slide deck travel.

Accordingly, by the use of the three slide deck components 104, 106, and 108, it is possible to translate the pyramid adaptor, and thus, the prosthesis socket 60 attached to the robotic prosthesis alignment device 101, to any coordinates in a two-dimensional or horizontal plane; thus, being able to adjust the lateral position of the prosthesis socket 60 in relation to the position of the prosthesis shank 30 and foot 20.

Figure 5:
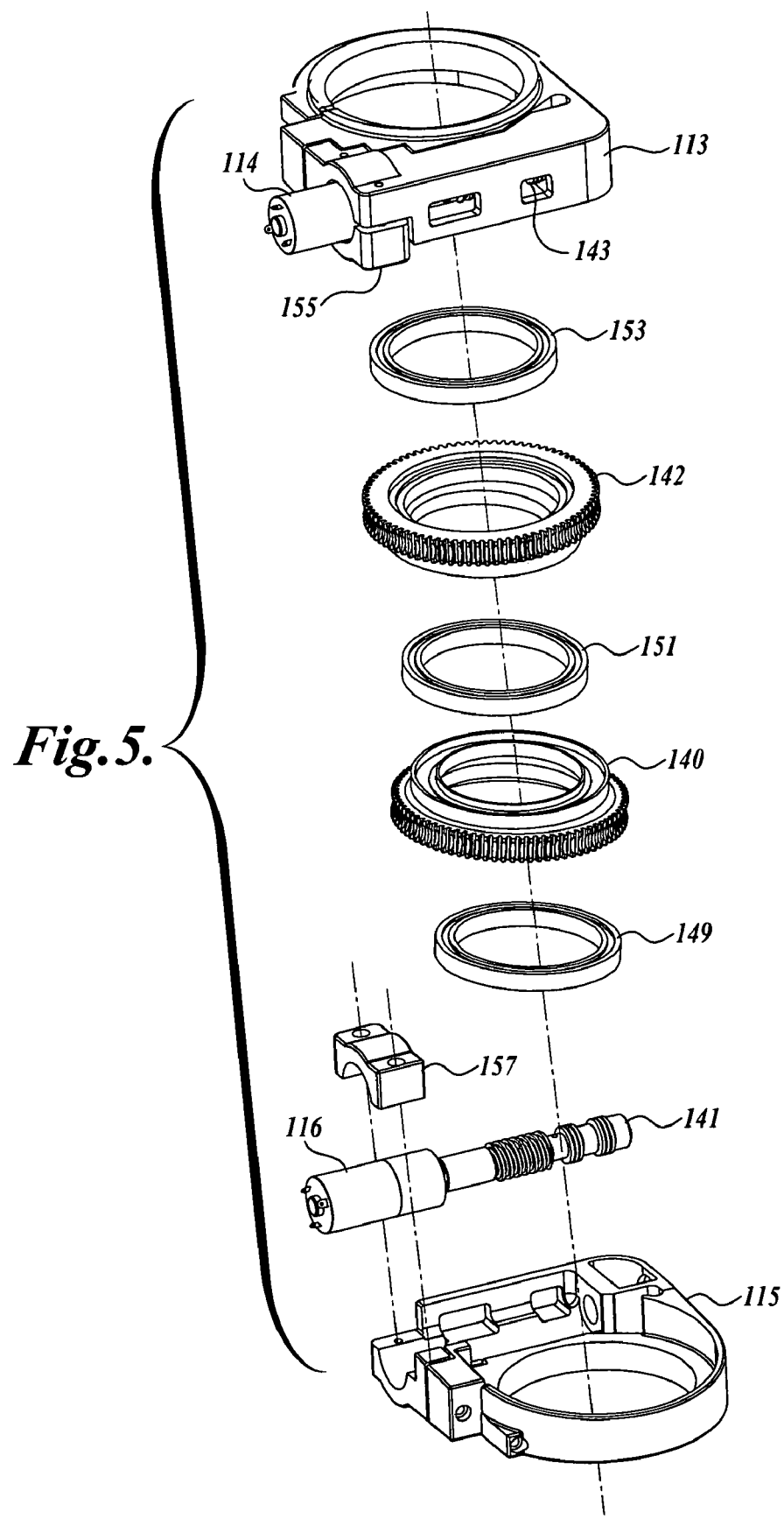
FIG. 5 is a diagrammatical illustration of an exploded view of a portion of the robotic prosthesis alignment device in accordance with one embodiment of the present disclosure.

Referring to FIGS. 2, 4, and 5, the robotic prosthetic alignment device 101 further includes first 110 and second 112 angulation decks comprising the angulation assembly. Each angulation deck includes a housing 113, 115, respectively, within which a worm gear is provided on a side thereof, the worm gears being supported by appropriate bearings in the housing. The worm gears 143, 141 are turned by drivers 114 and 116, respectively. Each housing further supports a robotic wedge 140 and 142 generally placed in the center thereof and adapted to rotate within the housing. The housing 113 of the upper angulation deck 110 has the wedge 142 supported on the lower slide of the housing 113, and the housing 115 of the lower angulation deck 112 has the wedge 140 supported on the upper side of the housing 115. As best seen in FIG. 5, the wedges 142, 140 are circular. Each wedge may be viewed as defining an upper side plane and a lower side plane, wherein the planes are angled with respect to each other. The upper side plane is separated from the lower side plane, thus, each wedge may be viewed as having a low point (or small height dimension) on one side thereof and a high point (or large height dimension) on the opposite side thereof. When placed on top of the other, the sum of the wedge height dimensions is cumulative and the individual wedge angles may increase the combined angle if the two high points and low points are aligned or the angles may cancel each other when the high point of one wedge is aligned with the low point of the other wedge, effectively resulting in no angle or an angle of 0°. Thus, the use of the pair wedges 140, 142 may be used to tilt a plane at any angle from 0° to the maximum angle when both high points are aligned. Further, because both circular wedges rotate, it is possible to effect such an angular position at any point of 360° of rotation. To enable rotation, each wedge 140, 142 has toothed gears around the circumference that mesh with the respective worm gear 141, 143. Each worm gear is driven by a driver. The driver 114 can rotate worm gear 143 and the driver 116 can rotate worm gear 141. Driver 114 is supported by motor mount 155 to the housing 113 and motor mount 157 supports driver 116 to the housing 115. Similar to drivers 117, 119 of the translation assembly, drivers 114 and 116 can include revolution counters that through the use of a computer and processor can measure the position of one wedge in relation to the other wedge. Each revolution can then correlate to an angle of tilting and to a position with respect to any degree of rotation to measure precisely how much angular adjustment and its direction at any time. For example, a revolution of zero may be assigned to both drivers 114, 116 when the wedges 140 and 142 are aligned such that the high point of one wedge is aligned to a low point of the other wedge, resulting in the minimum angle of tilt possible. For each revolution or number of revolutions of each driver 114, 116, the resulting angle can be recorded and a database can be generated of the angle, the position with respect to the front to back and side to side planes, and the revolutions of each driver 114, 116. Thus, to arrive at a certain angle of tilting of the prosthesis, the drivers 114, 116 can be commanded to a certain revolution. Alternatively to counting revolutions, sensors can be used to determine the position of one wedge with respect to the other. To further enable rotation of the wedges 140, 142, a turntable bearing 151 is provided between the interface of the lower surface of the upper wedge 142 and the upper surface of the lower wedge 140. The upper surface of the upper wedge 142 is further in contact with the bottom surface of the housing 113 via a second turntable bearing 153. The lower surface of the lower wedge 140 is further in contact with the upper surface of the housing 115 via a third turntable bearing 149. Accordingly, both the lower wedge 140 and the upper wedge 142 are permitted to rotate independently within their respective housing 115, 113 without causing rotation of the pyramid adaptor on top and tube clamp adaptor 40 below. As mentioned before, each angulation deck 110, 112 includes a worm gear that is coupled to a toothed gear provided around the circumference of each of the wedges. As the drivers rotate one or both of the wedges, the angle of tilting and its direction can be controlled. Combining different positions of the wedges 140, 142 varies the side-to-side angle and the front-to-back angle. Both the upper 142 and the lower 140 wedges may include a graduated scale along the periphery so that the position of one wedge with respect to the other can be visually read. A surrogate device, as further discussed below, can have wedges 1402, 1404 that tilt when rotated similar to the wedges 140, 142, and can be used to transfer the angular alignment. These surrogate wedges 1402, 1404 can have a graduated scale similar to the scale used in the wedges 140, 142. Using the reading obtained from the wedges 140, 142, the numerals on the scales of the surrogate wedges can be configured to line up similarly thus producing a similar alignment to the robotic prosthesis alignment device 101. Any non-dimensional or dimensional units, such as degrees, can be used to measure the location of one wedge with respect to the other and with respect to the housings. Alternatively, the position of the wedge rings may be determined via a computer and processor. The latter may be accomplished by counting the revolutions of the drivers 114 and 116 and correlating specific combinations of revolutions of each driver to a degree of tilting and to its direction. Alternatively sensors, such as a magnetic sensors can be used to measure the position of the two wedges. Alternatively to having graduated scale on the wedges 140, 142, the computer may provide a dimensionless number or numbers that defines the position of the wedge 140 to the position of the wedge 142. These numbers provided by the computer can then be used to align to surrogate wedges 1402, 1404.

Figure 6:
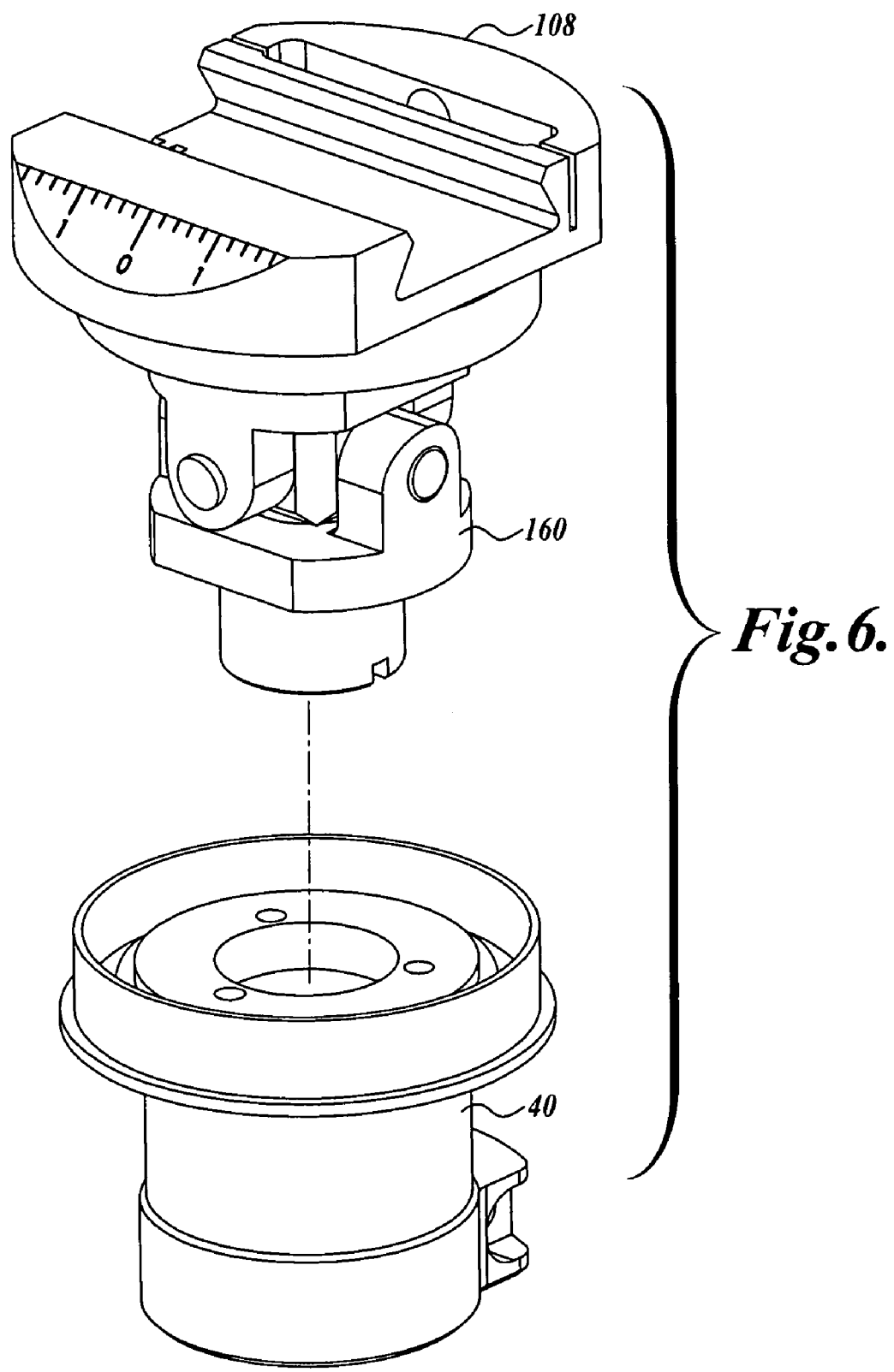
FIG. 6 is a diagrammatical illustration of an exploded view of a portion of the robotic prosthesis alignment device in accordance with one embodiment of the present disclosure.

Because the wedges cause tilting during rotation, the translation assembly which is positioned on the top of the upper angulation deck 110 is tilted along with the angulation assembly. To that end, and referring to FIG. 6, the bottom slide deck 108 of the translation assembly is connected via a universal joint 160 to the tube clamp adaptor 40. As shown in FIG. 5, the housings 113, 115, the wedges 140, 142, and the bearings 149, 151, 153, all have center bores allowing the passage of the universal joint therethrough.

Figure 7:
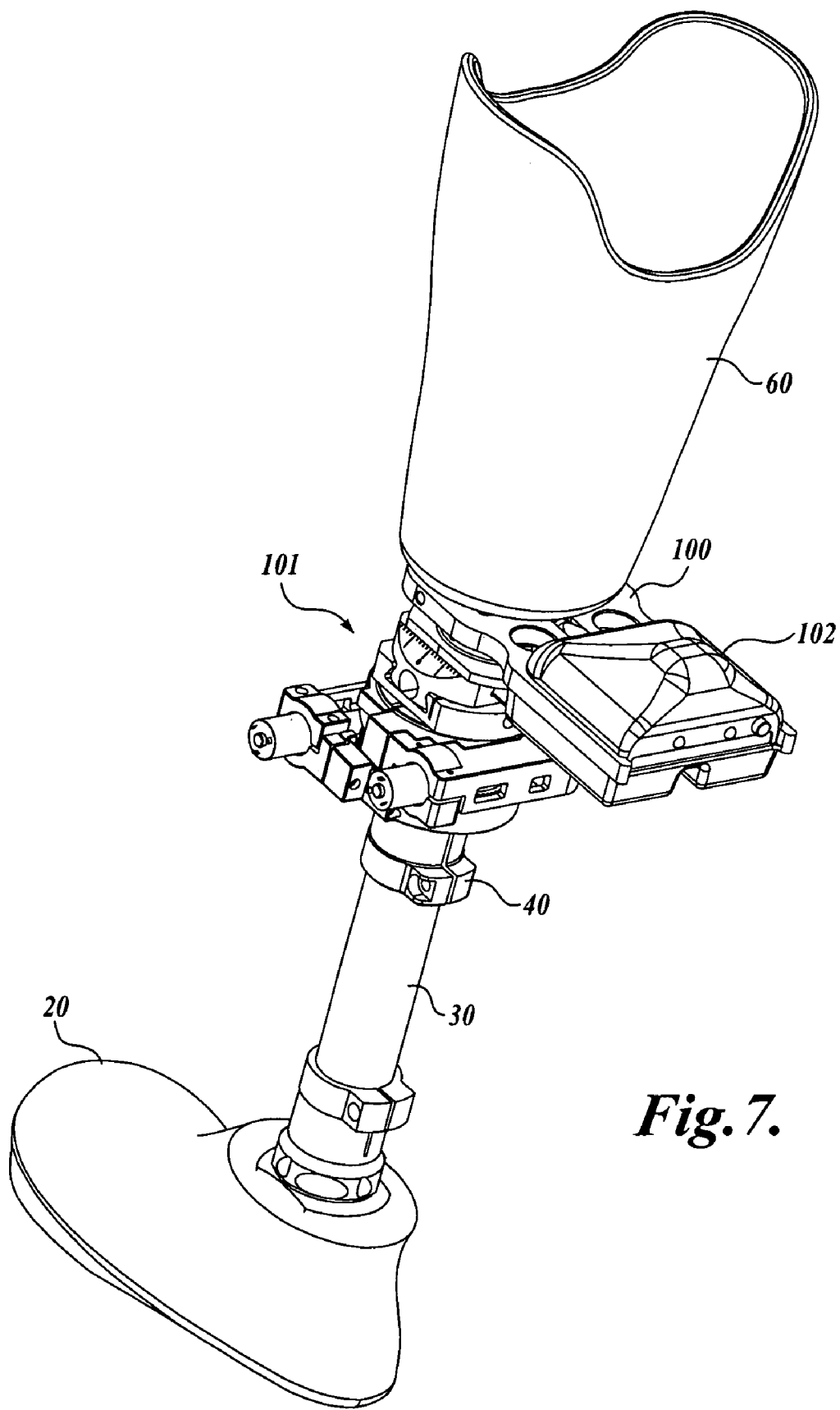
FIG. 7 is a diagrammatical illustration of the robotic prosthesis alignment device incorporated into a prosthesis including a prosthesis shank, prosthesis foot, and prosthesis socket in accordance with one embodiment of the present disclosure.

Referring to FIG. 7, the robotic prosthesis alignment device 101 is shown incorporated into a prosthesis to connect the prosthesis socket 60 to the prosthesis tube clamp adaptor 40. While FIG. 7 shows the torque sensor 100 and module 102 also attached to the prosthesis, it is not necessary to use the torque sensor 100 and module 102 simultaneously with the robotic prosthesis alignment device 101. Further, although the robotic prosthesis alignment device 101 is shown at the joint between the prosthesis socket 60 and prosthesis shank 30, the robotic prosthesis alignment device 101, as well as the torque sensor 100 and module 102, can also be located at the joint between the prosthesis shank 30 and the prosthesis foot 20, as well as having two robotic prosthesis alignment devices, one at the joint between the socket and shank and the other at the joint between the shank and foot. Placing the robotic prosthesis alignment device 101 at the joint between foot 20 and shank 30 might be desirable because small angular movements are not magnified by the length of the shank 30.

Figure 8:
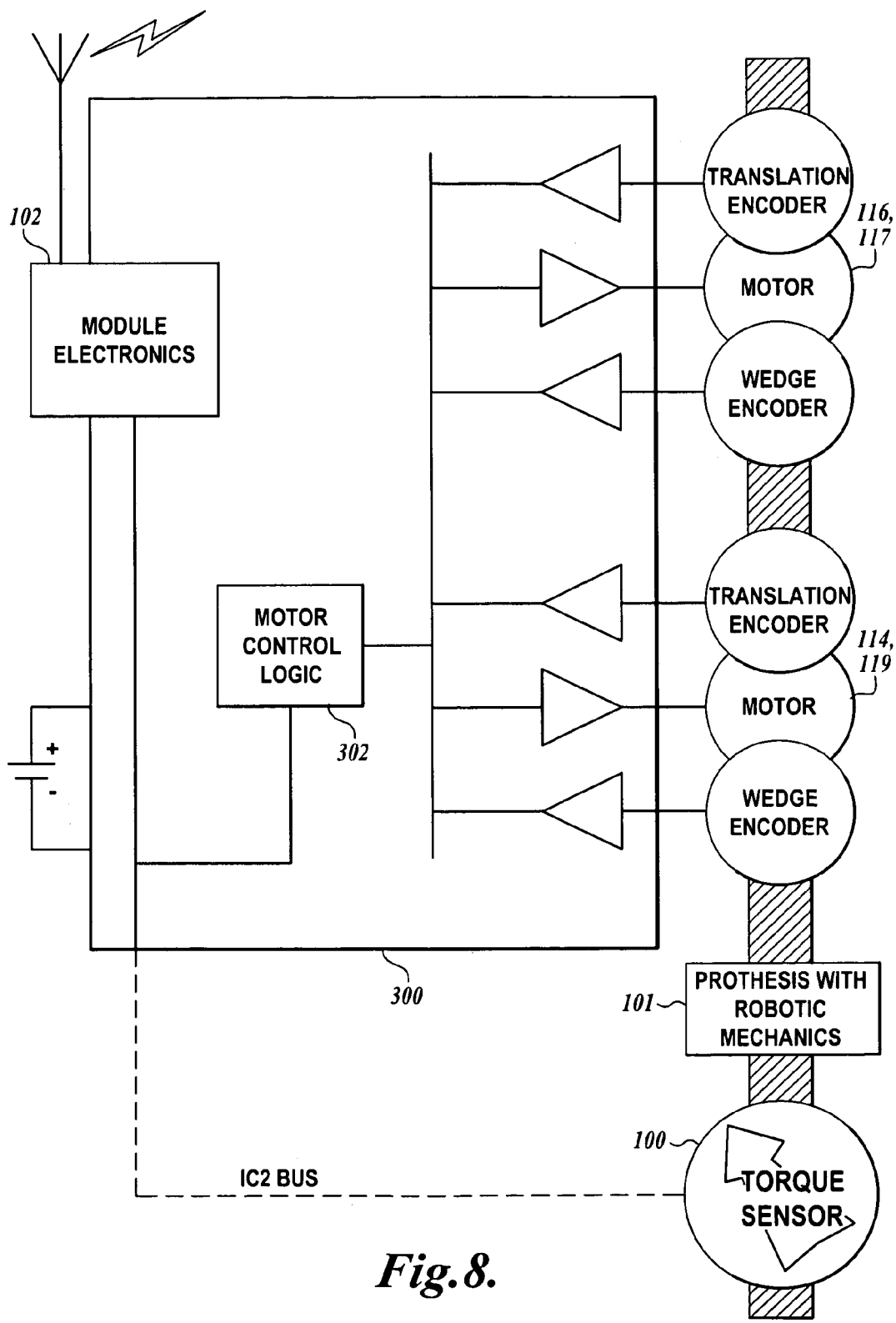
FIG. 8 is a schematic illustration of the control scheme of a computer device in communication with the robotic prosthesis alignment device in accordance with one embodiment of the present disclosure.

Referring to FIG. 8, a schematic block diagram of the robotic prosthesis alignment device's 101 electronic connections is illustrated. As a point of reference FIGS. 7 and 8 of the prior publications schematically illustrate the electronics of the torque sensor 100 and module 102 and will not be illustrated herein for brevity. The computer disclosed in the prior publications or a different computer 300 can be communicatively coupled to the torque sensor 100 and module 102, and further capable of running prosthesis alignment software as disclosed in the referenced publications, as well as also communicating with the robotic prosthesis alignment device 101 disclosed herein. The computer device 300 can be a handheld computer, such as a PDA, and is used to provide the motor control logic 302 that drives the individual drivers 114, 116, 117 and 119 that determine the setting of the transverse sliding decks and also to set the angle using the angulation decks. Alternatively, the computer device 300 may also be an embedded processor. The drivers 114, 116, 117, 119 are communicatively coupled to encoders that are further coupled to the computer 300. The motor control logic 302 uses hardware that takes position data from the encoders, compares the current position using software running on computer 300 against the position goal from the computer 300 software and drives the motors until the position goal and encoder outputs match. The computer 300 may be a personal digital assistant (PDA) and may have wireless transmission capability, such as Bluetooth®. The PDA can transmit instructions to the robotic prosthesis alignment device 101 to tilt the prosthesis socket in one or both planes and to translate the prosthesis socket in orthogonal directions. The computer 300 software, such as running on a PDA, can make decisions and run significant algorithms relating to the translation and rotation of the translating decks and wedges.

The applications running the robotic prosthesis alignment device 101 may be described in the context of computer-executable instructions, such as program modules being executed by the host computer 300. The computer-executable instructions or applications may be stored on one or more computer readable medium, such as, but not limited to hard drives, memory, disks, and the like. Generally described, program modules include routines, programs, applications, objects, components, data structures and the like, that perform tasks or implement particular abstract data types. The following description provides a general overview of the computer 300 with which the method for automatically aligning a prosthesis may be implemented. Then, the method for automatically aligning the prosthesis will be described, including the use of applications on the computer. The illustrative examples provided herein are not intended to be exhaustive or to limit the invention to the precise forms disclosed. Similarly, any steps described herein may be interchangeable with other steps or a combination of steps or, be arranged in a different sequence in order to achieve the same result.

Figure 9:
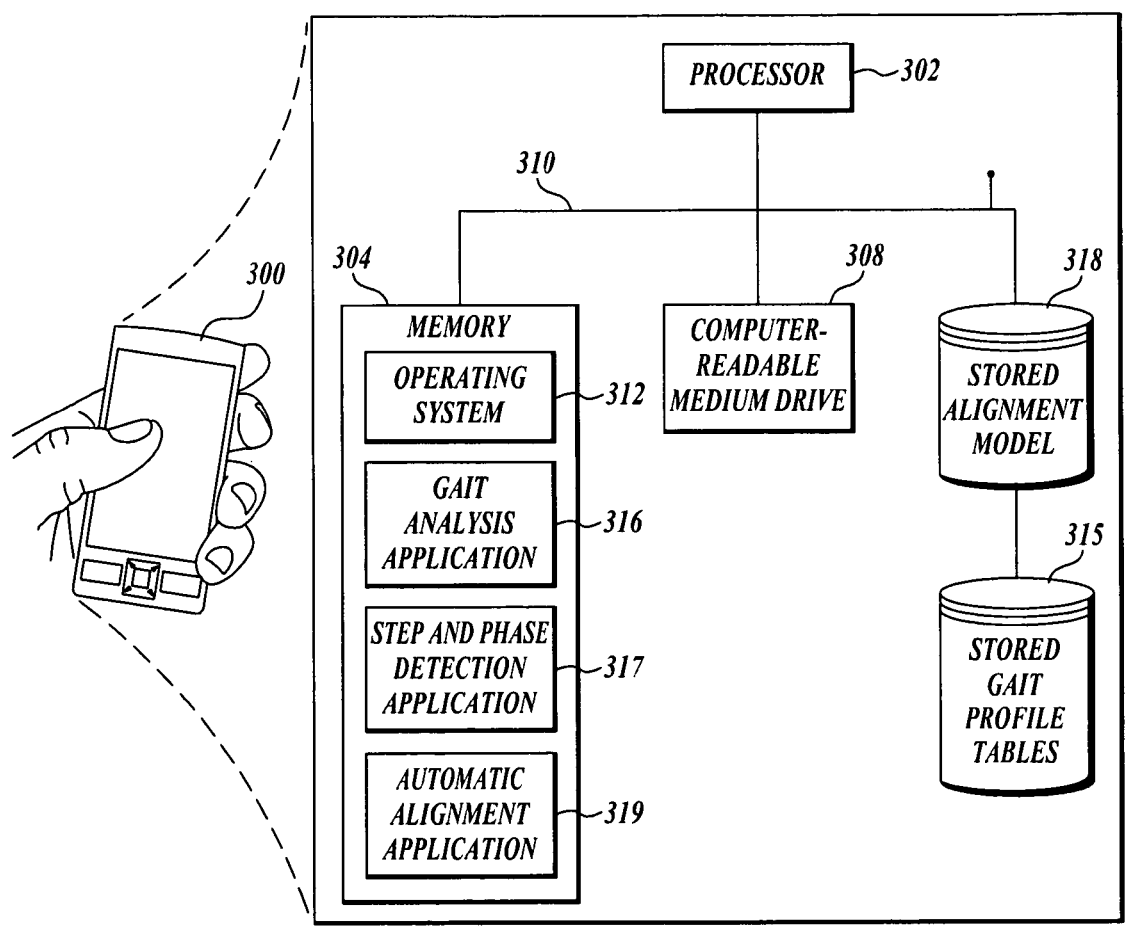
FIG. 9 is a diagrammatical illustration showing a representative computer used with the robotic prosthesis alignment device in accordance with one embodiment of the present disclosure.

FIG. 9 illustrates an exemplary host computer 300 with components that are capable of implementing an automatic method to align a prosthesis by conducting "gait analysis". The gait analysis application 316 and the phase and step detection application 317 have been illustrated and disclosed in the prior publications and will not be described herein for brevity. The gait analysis application 316 and the phase and step detection application 317 can be used to generate a database 315 of profiles of gait cycles correlating to each lateral position and each angular position attainable with the robotic prosthesis alignment device 101. However, once the database 315 is created, a user of the robotic prosthesis alignment device 101 need not use the gait analysis application 316 and the phase and step detection application 317 for automatically performing self-alignment of the prosthesis as further disclosed below.

Those skilled in the art and others will recognize that the host computer 300 may be any one of a variety of devices including, but not limited to, personal computing devices, server-based computing devices, mini and mainframe computers, laptops, or other electronic devices having some type of memory. The host computer 300 can also be an embedded processor located on the robotic prosthesis alignment device 101. The host computer 300 depicted in FIG. 12 includes a processor 302, a memory 304, a computer-readable medium drive 308 (e.g., disk drive, a hard drive, CD-ROM/DVD-ROM, etc.), that are all communicatively connected to each other by a communication bus 310. The memory 304 generally comprises Random Access Memory ("RAM"), Read-Only Memory ("ROM"), flash memory, and the like.

As illustrated in FIG. 9, the memory 304 stores an operating system 312 for controlling the general operation of the host computer 300. The operating system 312 may be a special purpose operating system designed for the computerized prosthesis alignment system 100. Alternatively, the operating system 312 may be a general purpose operating system, such as a Microsoft® operating system, a Linux operating system, or a UNIX® operating system. In any event, those skilled in the art and others will recognize that the operating system 312 controls the operation of the host computer 300 by, among other things, managing access to the hardware resources and input devices. For example, the operating system 312 performs functions that allow a program to receive data wirelessly over a radio receiver and/or read data from the computer-readable media drive 308. As described in further detail below, moment and axial load data in real time may be made available to the host computer 300 from the master unit module 102 and from the computer-readable medium drive 308. In this regard, a program installed on the host computer 300 may interact with the operating system 312 to process the data received from one or both the master unit module 102 and the computer-readable media drive 308.

As further depicted in FIG. 9, the memory 304 additionally stores program code in the form of applications. The gait analysis application 316 includes computer-executable instructions that, when executed by the processor 302, applies an algorithm to receive, display, and process input, including moment and axial load data. The gait analysis application 316, among other things, applies an algorithm to a set of moment data to correct for any horizontal rotational deviation of the torque sensor 100 during walking to the actual line of progression and then compares the corrected data to an optimal model of alignment stored on a device 318. The step and phase detection application 317 applies an algorithm to a set of moment and axial data to determine if the prosthesis is being used in steady state walking, and if it is, the algorithm differentiates each step on the prosthesis and extracts the moment data beginning each step at initial contact and ending each step at the following initial contact in the gait cycle. Further, the step and phase detection application 317 establishes if the prosthesis is either in stance or swing phase of a gait cycle at each data point extracted for each step. The gait analysis application 316 and the phase and step detection application 317 have been illustrated and disclosed in the prior publications and these applications may be implemented by the host computer 300 disclosed herein or by a different computer to generate that database 315 mentioned above. Self or automatic alignment is a goal of methods disclosed herein. The self-aligning automatic alignment application 319 performs a set of operations, without the use of the torque sensor 100 and module 102 that can automatically align the prosthesis with the use of the drivers. The application 319 is described in association with the flow diagram of FIG. 17 below.

Figure 10:
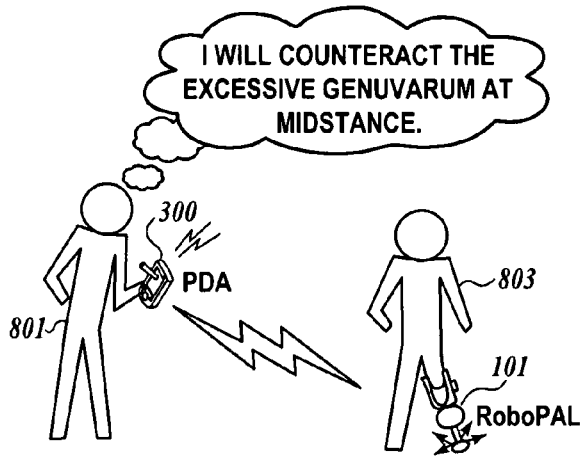
FIG. 10 is a diagrammatical illustration showing a first operational mode of the robotic prosthesis alignment device in accordance with one embodiment of the present disclosure.
Figure 11:
FIG. 11 is a diagrammatical illustration showing a second operational mode of the robotic prosthesis alignment device in accordance with one embodiment of the present disclosure.
Figure 12:
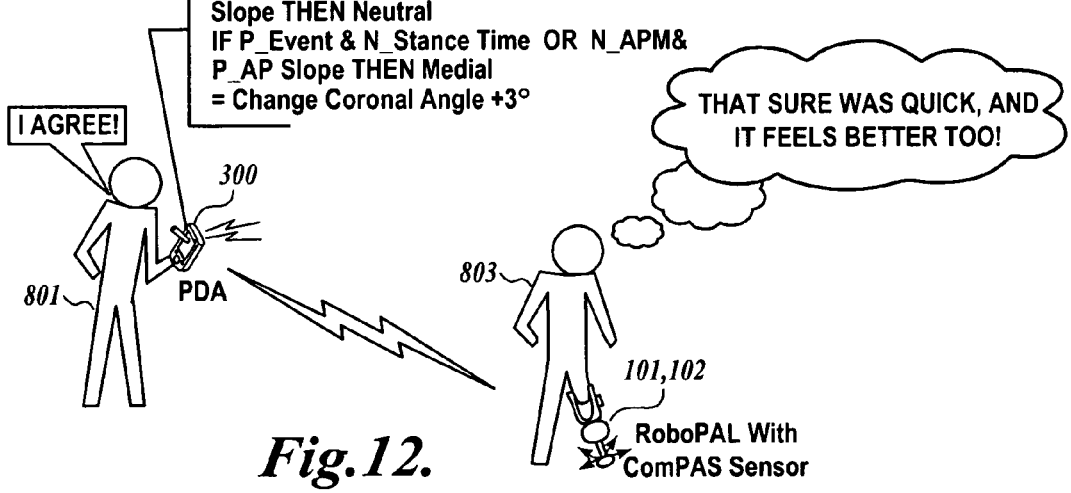
FIG. 12 is a diagrammatical illustration showing a third operational mode of the robotic prosthesis alignment device in accordance with one embodiment of the present disclosure.

Referring to FIGS. 10, 11, and 12, the computer 300 may operate in one of three modes. A first mode (FIG. 10) is for the robotic prosthesis alignment device 101 to interface with a prosthetist 801 with the use of a computer 300, a second mode (FIG. 11) is for the user 803 to interface with the robotic prosthesis alignment device 101 with the computer 300, and the third mode (FIG. 12) is for the robotic prosthesis alignment device 101 to interface automatically with a computer, such as computer 300, either with user interface or without user interface, such as in a self-aligning automatic mode.

Figure 13:
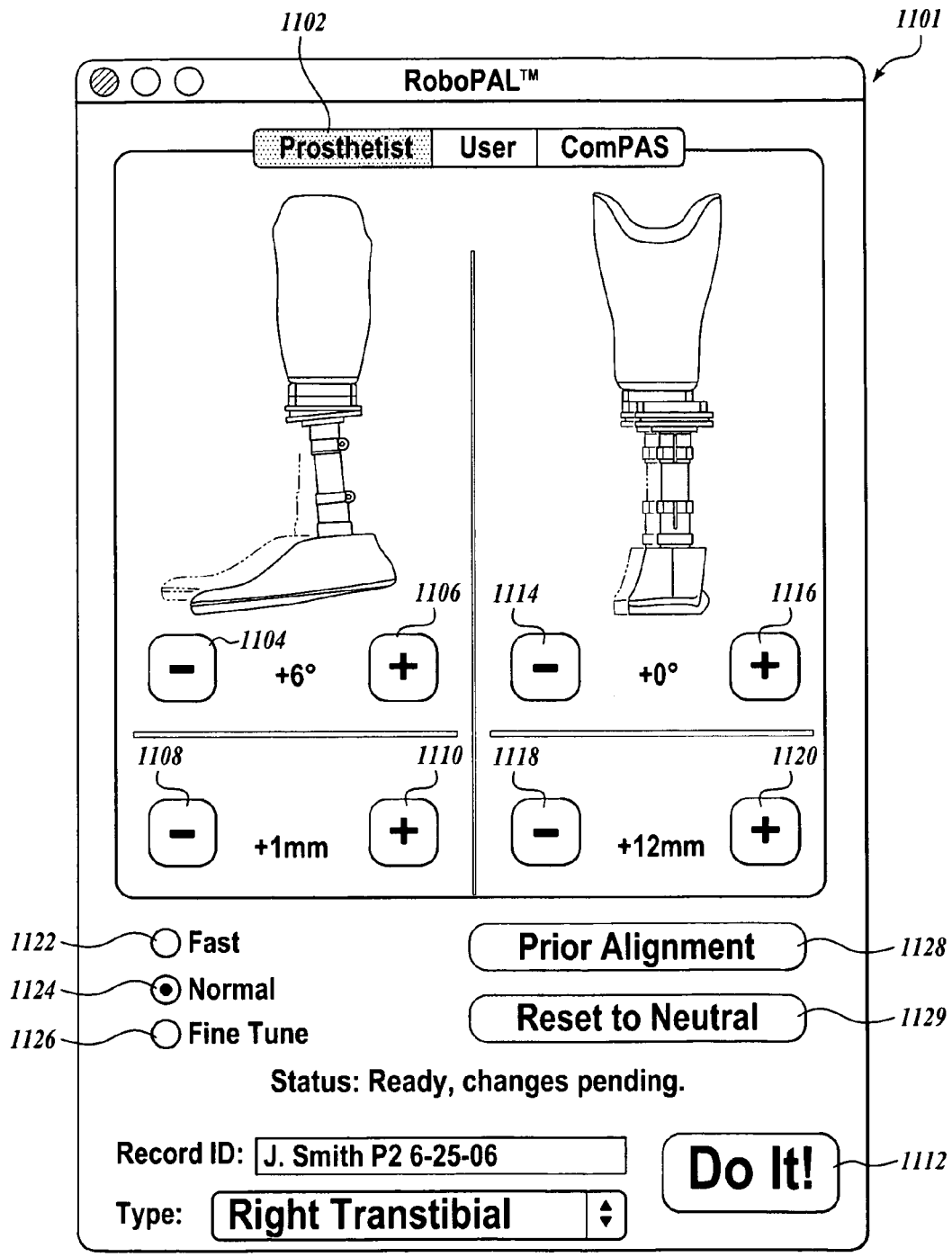
FIG. 13 is a diagrammatical illustration of a graphical user interface of the first operational mode of the robotic prosthesis alignment device in accordance with one embodiment of the present disclosure.

FIG. 13 is an illustration of a representative graphical user interface 1101 for the first mode. The interface 1101 includes buttons 1102 used for selecting between prosthetist, user, and the computerized prosthesis alignment system. In FIG. 13, the prosthetist button is highlighted, indicating that the graphical user interface is customized for a prosthetist. The graphical user interface 1101 presents to the prosthetist, a figure illustrating both a side view and a front or back view of the prosthesis, including the socket, the robotic prosthesis alignment device 101, and the shank and foot. Referring to the left side of the figure, in the side view, the prosthetist is able to view the forward or backwards translation and also the front/back angle. The prosthetist is presented with a minus button 1104 and a plus button 1106 for adjusting the pitch angle or the front to back angle. Selecting the minus button 1104 decreases the angle. Alternatively, selecting the plus button 1106 will increase the angle. The prosthetist is presented with a minus button 1108 and a plus button 1110 for adjusting the forwards and backwards translation. Selecting the minus button 1108 decreases the distance that the shank with foot translates backwards. Alternatively, selecting the plus button 1110 increases the distance that the shank with foot translates forwards. When the prosthetist is satisfied with the settings, the prosthetist can select a DO IT button 1112, and the changes are executed by the robotic prosthesis alignment device 101. Referring to the right side of the figure, in the front or back view, the prosthetist is able to view the side-to-side translation and also the roll angle or the side to side angle. The prosthetist is presented with a minus button 1114 and a plus button 1116 for adjusting the angle. Selecting the minus button 1114 decreases the angle. Alternatively, selecting the plus button 1116 will increase the angle. The prosthetist is presented with a minus button 1118 and a plus button 1120 for adjusting the side translation. Selecting the minus button 1118 will decrease the distance that the shank with foot will translate medially (towards the middle of the body). Alternatively, selecting the plus button 1120 will increase the distance that the shank with foot will translate laterally (towards the outside of the body). When the prosthetist is satisfied with the settings, the prosthetist can select the DO IT button 1112, and the changes are executed by the robotic prosthesis alignment device 101. The graphical user interface 1101 also presents to the prosthetist choices for the responsiveness of movements. The user is presented with a fast 1122, normal 1124 and fine tune 1126 button to select responsiveness from the robotic prosthesis alignment device 101. The graphical user interface 1101 may present a prior alignment button 1128. By selecting the prior alignment button 1128, the computer supporting the graphical user interface recalls from memory the immediate prior alignment. The graphical user interface 1101 may present a Reset to Neutral button 1129. By selecting the Reset to Neutral button 1129, the robotic prosthesis alignment device may return all alignments to the home or neutral position.

Figure 14:
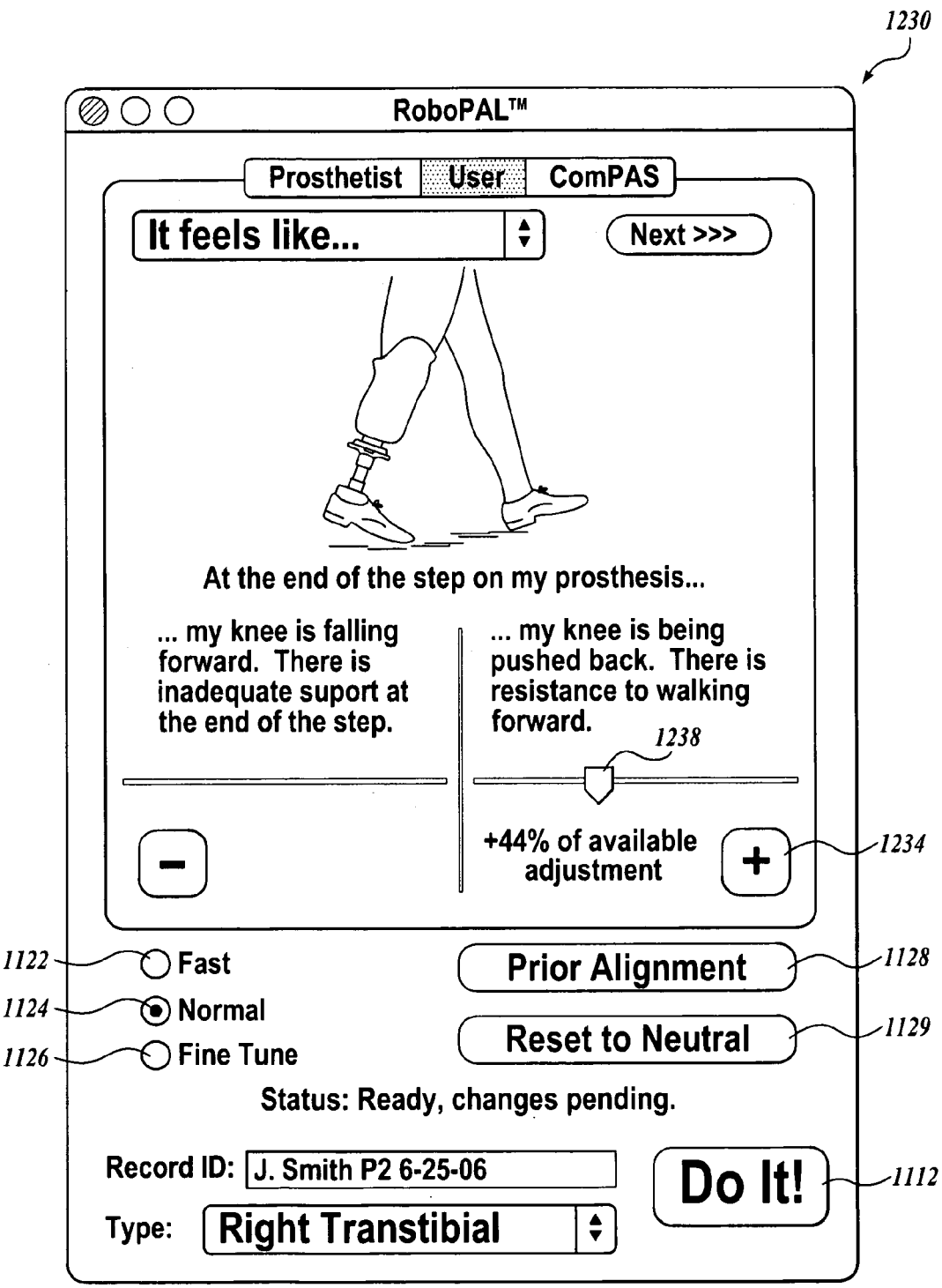
FIG. 14 is a diagrammatical illustration of a graphical user interface of the second operational mode of the robotic prosthesis alignment device in accordance with one embodiment of the present disclosure.

FIG. 14 is an illustration of a representative graphical user interface 1230 for the second mode for a user, i.e., the wearer, of the prosthesis. The graphical user interface 1230 may present to the user a sensation-oriented interface. In this mode, the graphical user interface will prompt the user regarding their sensations during walking, such as whether the user feels their knee was being pushed in a certain direction as they stepped on the prosthesis. In one embodiment, the graphical user interface 1230 presents to the user a series of questions concerning the sensations that the user is experiencing to which the user can reply by selecting a minus button 1232 or a plus button 1234. For instance, one example of a question presented to a user may read, "At the end of the step on my prosthesis . . . ?" And the response can be a selection of two options; "my knee is falling forward. There is inadequate support at the end of the step" or, "my knee is being pushed back. There is resistance to walking forward." By selecting the negative button 1232 or the plus button 1234, the user can select which of the two options most closely matches the sensation being felt. Selecting the plus button 1234 moves the pointer 1236 in the direction of the second sensation, while selecting the minus button 1232 moves the pointer 1236 in the direction of the first sensation. The range of the pointer might coincide with the range of available adjustment, i.e., either the translational or angular adjustment or both. In this manner, the user provides a response that correlates most closely to the actual sensation being experienced by the user. When the changes have been entered, the user may select the DO IT button 1112 and the changes are executed by the robotic prosthesis alignment device 101.

Figure 15:
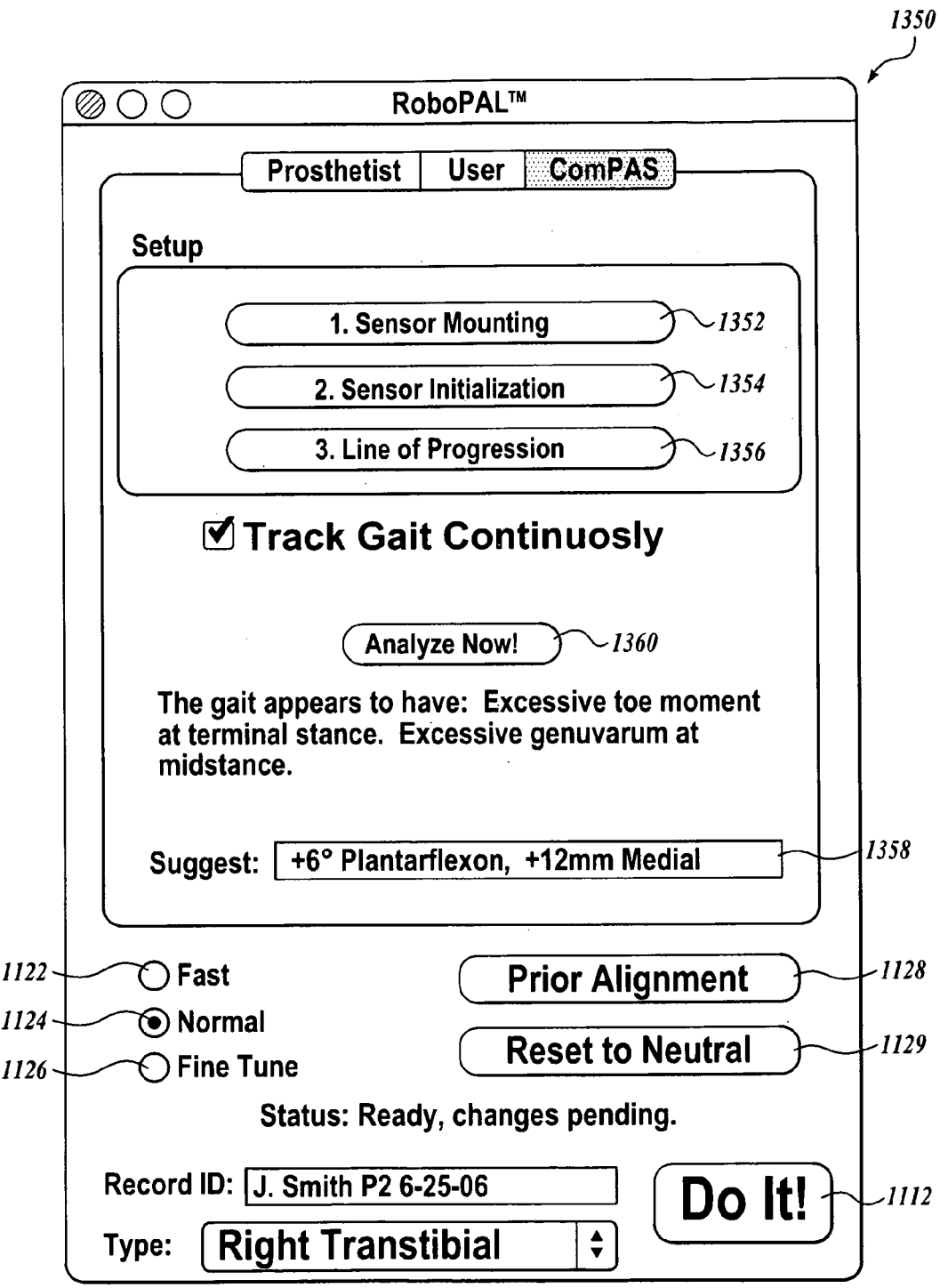
FIG. 15 is a diagrammatical illustration of a graphical user interface of the third operational mode of the robotic prosthesis alignment device in accordance with one embodiment of the present disclosure.

FIG. 15 is an illustration of a graphical user interface 1350 for the third mode when the computer 300 operates the robotic prosthesis alignment device 101. The graphical user interface 1350 may present a setup page. In the setup page, the graphical user interface 1350 may present a Sensor Mounting button 1352, a Sensor Initialization button 1354, and a Line of Progression button 1356. These operations have been disclosed in the referenced publications. The graphical user interface 1350 may perform the alignment method as disclosed in the above-referenced applications by selection of the Analyze button 1360. This alignment method uses the gait analysis application 316 and the step and phase detection application 317 already disclosed in the referenced publications. However, in the present disclosed graphical user interface 1350 herein, instead of presenting the user or prosthetist with instructions on turning the set screws, the graphical user interface 1350 may present a suggestion 1358, such as degrees of plantarflexion, dorsiflexion, inversion, eversion and/or distance of translation in either the lateral or medial direction. By selecting the DO IT button 1112, the suggestion is executed by the robotic prosthesis alignment device 101. Furthermore, the suggestions generated by the disclosed method can be implemented automatically to provide a self-aligning prosthesis. A self-aligning prosthesis will not depend on the person to execute the movement to align the prosthesis, but will automatically move the prosthesis to the selected alignment. The self-aligning prosthesis option can be turned off by the user if desired. The method disclosed herein for providing suggestions that are executed by the person or automatically is described in association with FIG. 17 below.

Figure 16:
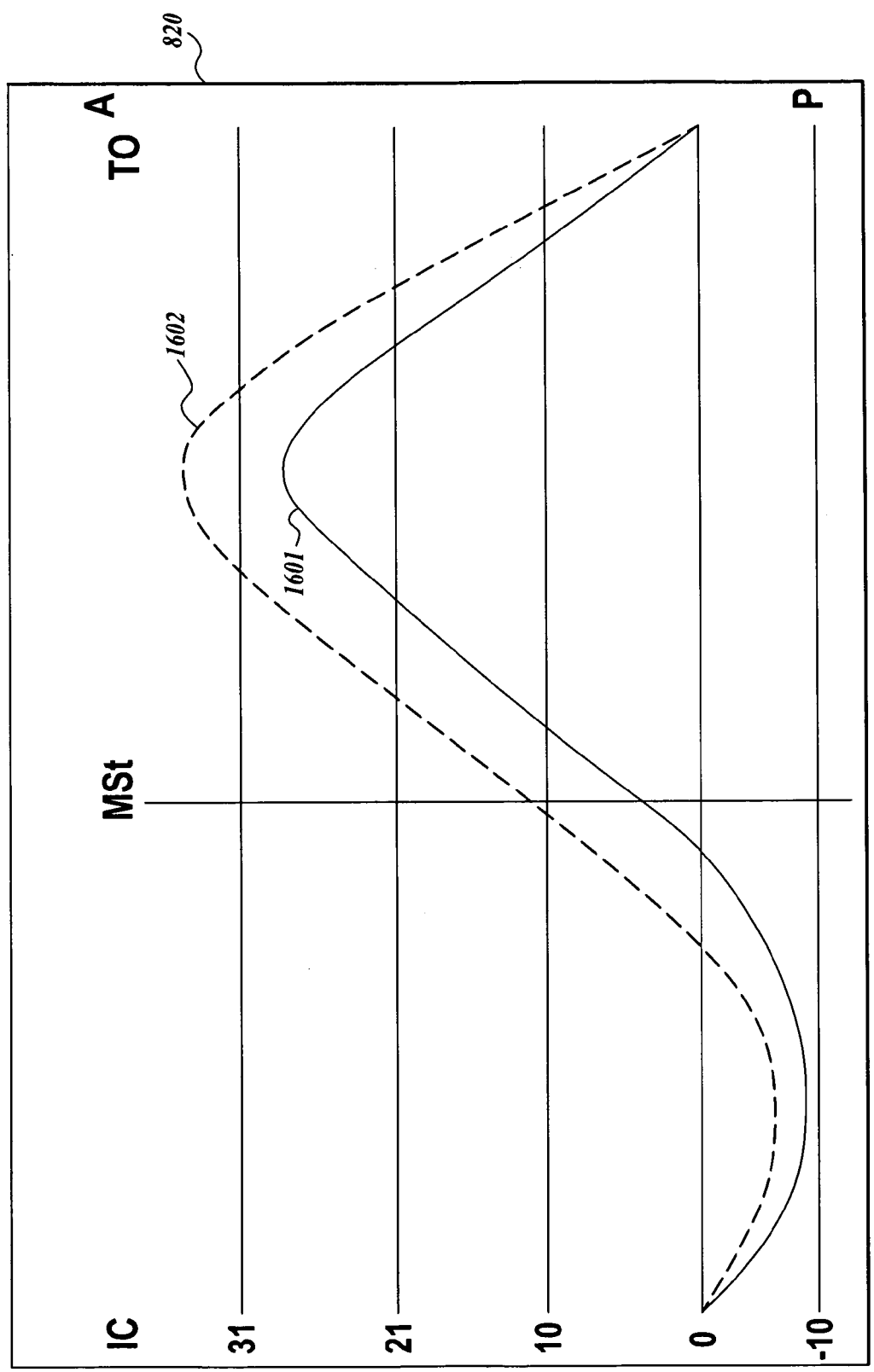
FIG. 16 is a graph showing a representative gait cycle profile of socket reaction forces along the anterior/posterior plane and a representative optimal gait cycle profile.

Before discussing the self-aligning method, a profile of a gait cycle is briefly described with reference to FIG. 16. A representative profile of a gait cycle is shown as curve 1601 in the anterior/posterior socket reaction graph. The right/left socket reaction graph may also be prepared for a gait cycle. A gait cycle profile represents a repeating unit of the walking motion, for example, from initial contact (IC) of the heel of one foot to the subsequent initial contact of the heel of the same foot. The gait cycle of one foot includes a stance phase when the foot is in contact with the ground. The gait cycle includes a swing phase when the foot is not in contact with the ground. Initial contact is the start of the stance phase when the heel makes contact with the ground. Toe-off (TO) is the end of the stance phase when the toe leaves the ground. The swing phase occurs after toe-off and before initial contact of the heel. One swing phase and one stance phase complete a gait cycle. There are torques associated with each gait cycle along the posterior to anterior and right to left. These torques can be measured by the torque sensor 100 disclosed in the prior publications. From these readings a gait cycle profile can be generated for anterior/posterior socket reaction forces and for right/left socket reaction forces plotted against the stance phase from initial contact to toe-off. A theoretical optimum gait cycle profile is disclosed in the prior publications. This optimum gait cycle profile is represented by curve 1602.

Figure 17:
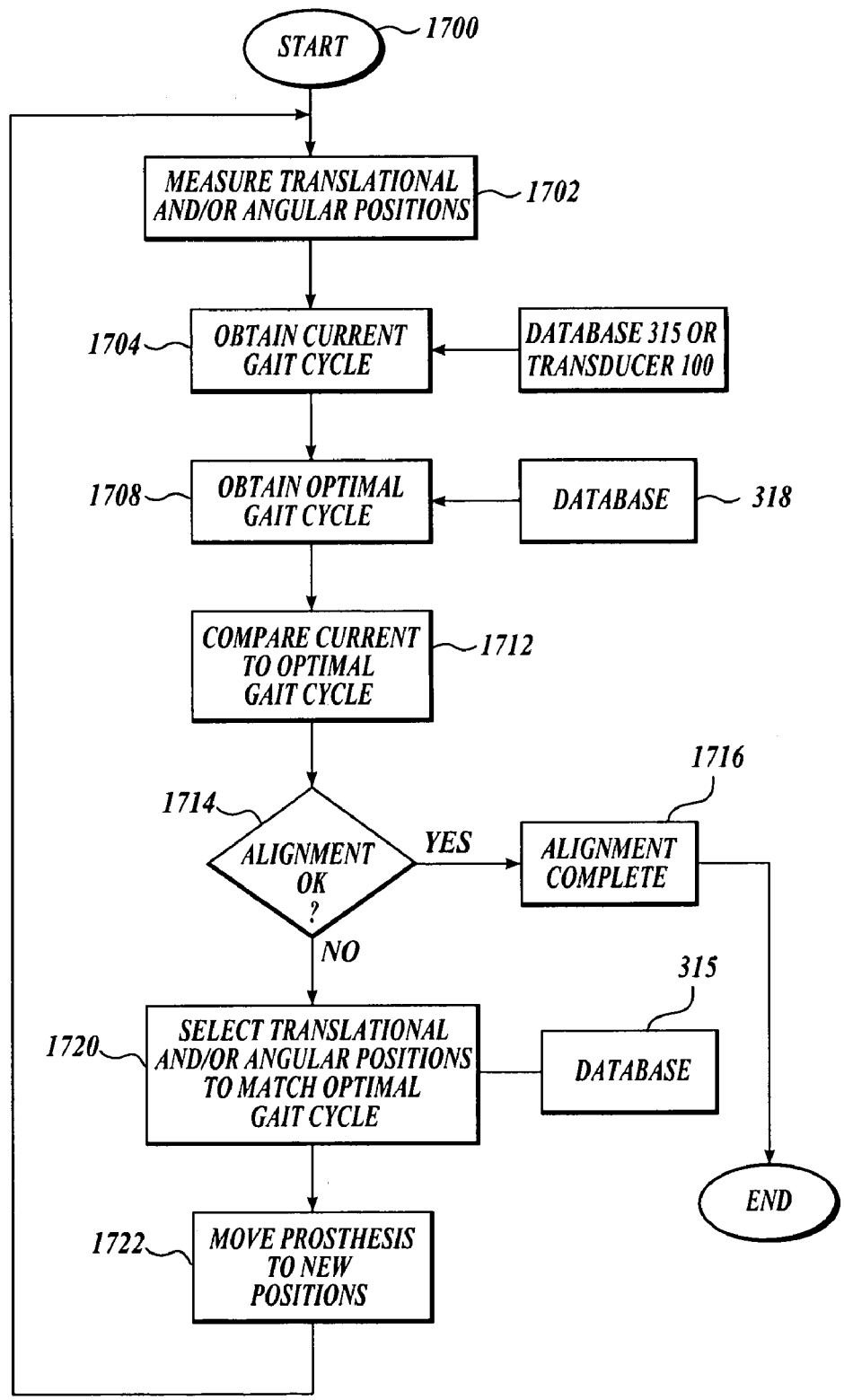
FIG. 17 is a flow diagram of a method for automatically performing self-alignment of a prosthesis.

Referring to FIG. 17, a method for automatically controlling the alignment of a prosthesis is schematically illustrated. FIG. 17 is a method that can automatically perform self-alignment of the prosthesis. The method starts at block 1700. From block 1700, the method enters block 1702. Block 1702 is for measuring the translational and/or angular positions of the current prosthesis alignment. For example, the translation assembly and the angulation assembly disclosed above may include various ways of determining the position by encoders, such as by counting the revolutions of a driver that moves a gear of either the translation assembly or the angulation assembly. In addition, a sensor may be mounted in a position on the translation assembly or the angulation assembly that provides a current position. From block 1702, the method enters block 1704. In block 1704, a current gait cycle is obtained. For example, the gait cycle can be obtained from the transducer 100 measuring torque forces and producing a real-time gait cycle using the gait analysis application 316 and the phase and step detection application 317. Alternatively, the database 315 of FIG. 9 can be accessed. The database 317 can contain a look-up table that correlates translational positions and angular positions to specific gait cycles. For example, the table can be generated beforehand, such as by moving the translation assembly throughout its range in both the two orthogonal directions and obtaining a profile of a gait cycle at each incremental adjustment while the angular adjustment is held constant. Once all the possible combinations of translations in two directions are determined for one angular position, the angular position can be changed one increment, and the range of translations is performed, until all possible translation and angular positions are tested. The profiles of gait cycles correlating to a specific angulation position can also be prepopulated in the database. For example, a gait cycle can be measured using the torque sensor for each incremental adjustment of a wedge. In the end, a database that has a profile of a gait cycle correlating to every translational position at every possible angle can be created. From step 1704, the method enters step 1708. In step 1708, an optimal profile of a gait cycle can be obtained. For example, the optimal gait cycle profile can be obtained from a database 318 (FIG. 9). The optimal gait cycle is calculated from the equations and methods disclosed in the prior publications.

From step 1708, the method enters step 1712. In step 1712, the current gait cycle is compared to the optimal gait cycle and a difference is determined that is defined as the misalignment. Various mathematical algorithms can be used to compare one plot of a gait cycle against another.

One embodiment for calculating the difference or misalignment between the current alignment and the optimal alignment may be to compare one or more of the gait variables against the alignment model calculated from a larger database of gait variables collected from multiple and different patients from numerous prior sessions and stored in the device of the host computer 300. To analyze for the misalignment, certain "gait" variables are calculated for a step. Gait variables may include, but are not limited to some or all of, the anterior/posterior moment and right/left moment at each 20 percent increment in time of the stance phase from 0% to 100%; the maxima and minima of the anterior/posterior moment and right/left moment for the first and the last 50% of the stance phase; the slope of the change in anterior/posterior moment and right/left moment during each successive 20% time increment; and the integrated anterior/posterior moment and right/left moment measured over the period of each stance phase. The gait variables are then applied to a predefined model of alignment. The equations used in deriving the model of alignment are derived heuristically to minimize an external criterion called the Prediction Error Sum of Squares, or PESS, for previously measured socket reaction moments and axial force with a known set of geometric misalignments.

$$PESS = \frac{1}{N}\sum_{t=1}^{N}(y_t - f(x_t, \hat{a}_t))^2$$

Where N is the number of gait variable samples available, y is the target geometric misalignment, and a is an estimation of the combined parameters that describe the misalignment. The equation derivations are achieved using the Group Method of Data Handling described by Madala and Ivakhnenko (Madala, H., and Ivakhnenko, A., "Inductive Learning Algorithms for Complex Systems Modeling," CRC Press, Boca Raton, Fla., USA, 1994). Solving the derived model equations with the gait variables calculated from the computerized prosthesis alignment system 100 data, results in a numeric estimation of the geometric misalignment in the prosthesis measured. For robustness, estimations from each of the equations becomes a vote added to a more generalized estimation of the misalignment.

From step 1712, the method enters step 1714. In step 1714, a determination is made as to whether the current gait cycle is acceptable in comparison to the optimal gait cycle. In block 1714, checking whether the alignment is okay might compare the current gate cycle to the optimal gate cycle and if the difference between the current gait cycle to the optimal gait cycle is below a threshold limit, the current gait cycle is identified as being acceptably close to the optimal gait cycle and the alignment is acceptable. If the determination is "yes," the method enters block 1716 and the alignment is complete, thus terminating the method. If the determination in block 1714 is "no," the method enters block 1720. In block 1720, the method selects a new transitional and/or angular position to match the optimal gait cycle. To select a new transitional and/or angular position to match the optimal gait cycle, the method can search the database 315 for a gait cycle that matches or approximates the optimal gait cycle. When the gait cycle is found, the look-up table will provide the translational coordinates and the angular coordinates that are correlated to the gait cycle. For example, this can be provided in the form of a number of driver revolutions corresponding to certain lateral and angular positions and/or to a voltage or resistance of a particular sensor corresponding to certain lateral and angular positions. Once the lateral and angular positions are know, these can be provided in the form of a suggestion 1358 as shown in FIG. 15 or the method can simply move the prosthesis automatically with the use of drivers without further input. From block 1720, the method enters block 1722. In block 1722, the computer 300 provides instructions to move the translation and angulation assemblies to the new positions. At this point, the method can terminate, thus assuming that the new positions will provide the closest match to the optimal gait cycle profile. Alternatively, the method can return to block 1702 and re-measure the translational and angular positions for verification and the method runs through steps 1704, 1708, 1712, and 1714 again to test whether the new position is in fact resulting in the desired optimal alignment.

Once an optimal alignment is achieved by any of the three modes, the robotic prosthesis alignment device 101 may need to be removed from the prosthesis along with the torque sensor 100. However, removal of the torque sensor 100 and the robotic prosthesis alignment device 101 should preferably be accomplished without losing the optimal alignment. To do this as disclosed in the prior publications, a substitute pyramid adaptor was used that had the same physical dimensions as the torque sensor. Two set screws were removed, which left two set screws in the optimal alignment position. With two set screws removed, the torque sensor/pyramid adaptor could be disassembled from the prosthesis. Thereafter, the substitute pyramid adaptor could be substituted for the torque sensor without losing the alignment. However, a drawback with this method is that the alignment cannot be transferred to a different prosthesis. Disclosed herein is a surrogate device that can be used to achieve the same alignment after the robotic prosthesis alignment device 101 is removed from the prosthesis. As disclosed herein, the robotic prosthesis alignment device 101 calculates the angular and translational positions and these can be provided as numerical indexes, either by visually inspecting the device once alignment is reached or the computer 300 may provide the angle and translation positions in units or numbers. The numerical indexes can be provided visually by viewing the positions of the translation and angulation assemblies via a index mark and a graduated scale or can be provided by computations performed by the computer 300 and displayed on a graphical user interface, such as shown in the suggestion box 1358 of FIG. 15. The numerical indexes then provide a means for transferring the alignment with the use of a surrogate device after the robotic prosthesis device 101 has been removed. The surrogate device is an intermediate component that connects that prosthesis shank to the prosthesis socket. The surrogate device is designed to duplicate the range of alignment that is achieved with the robotic prosthesis alignment device 101 and can directly replace the geometry of the robotic prosthesis alignment device 101.

Figure 18:
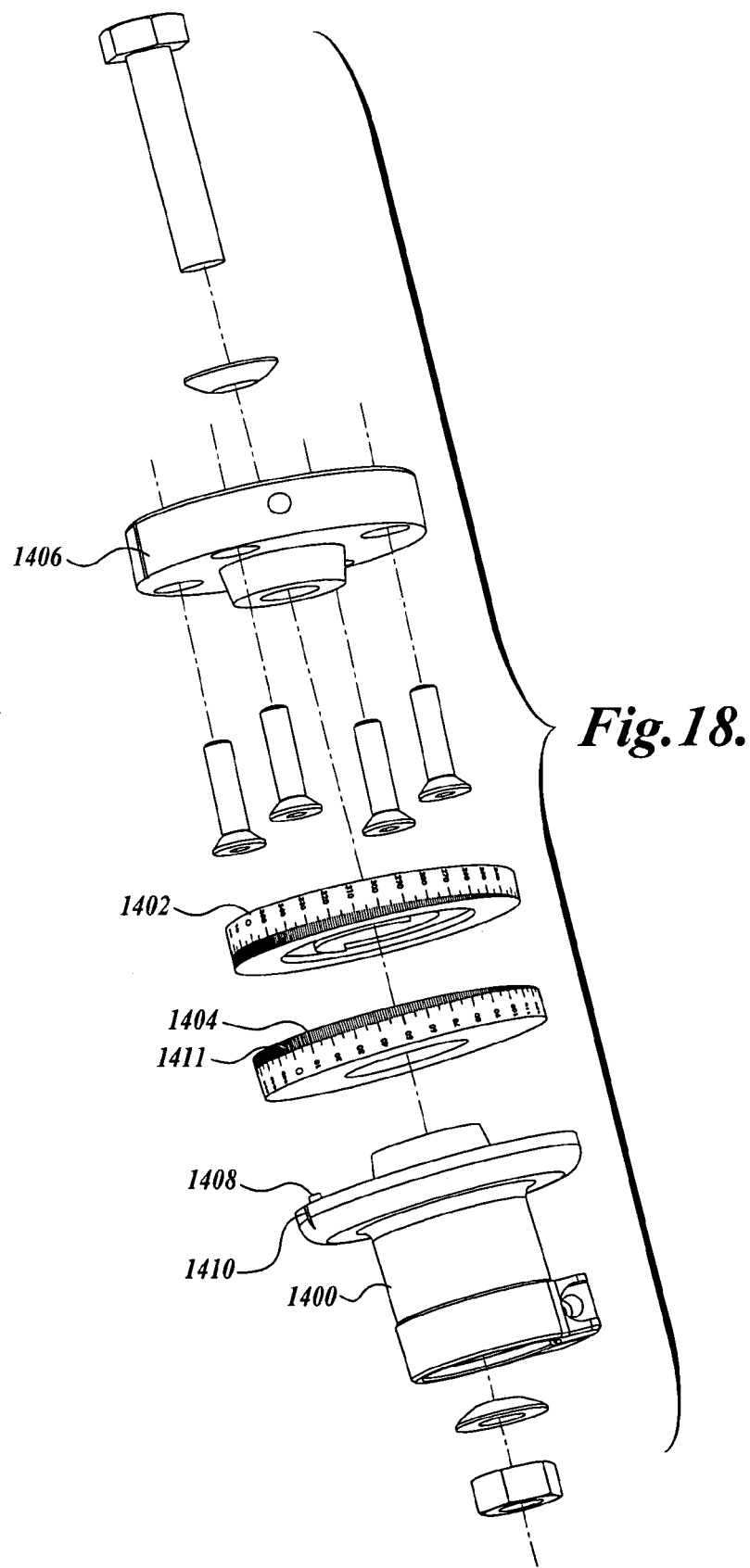
FIG. 18 is a diagrammatical illustration of an exploded view of a surrogate device in accordance with one embodiment of the present disclosure.

Referring to FIG. 18, the surrogate device includes a modified tube clamp adaptor 1400, a first wedge 1402 and second 1404 wedge, and a top coupling plate 1406. The wedge rings 1402 and 1404 can be color coded and made by injection molding a ultrahigh molecular weight polyethylene or a similarly appropriate resin. The tube clamp adaptor 1400 includes an upper surface designed to mate to the bottom surface of the wedge ring 1404. The tube clamp adaptor 1400 can be attached to the prosthesis shank. Each of the wedge rings 1402, 1404 includes a graduated scale 1411 along the circumference. The wedge rings 1402, 1404 have a low point and a high point that is directly opposite from the low point. One major surface of each wedge ring 1402, 1404 includes interlocking features. When assembled, the interlocking surfaces of the wedges 1402, 1404 are positioned against each other. The robotic prosthesis alignment device 101 includes wedges that could rotate in relation to one another to set the angular adjustment of the prosthesis. The wedges of the robotic prosthesis alignment device 101 may include indices on the circumference of the wedge rings that coincide with the indices of the wedges 1402, 1404 of the surrogate. In this manner, once alignment is completed, the indices are visually read from the robotic prosthesis alignment device 101 directly from the wedges 140 and 142 and then, the surrogate wedges 1402, 1404 are aligned so that the indices of the surrogate wedges 1402, 1404 are in the same alignment as the wedges 140, 142 to duplicate the angular adjustment. In another embodiment, the computer 300 includes software that can calculate the dimensionless indices to be used in the surrogate that match the angular alignment deemed to be optimal. For example, degrees of angular adjustment can be correlated to a numerical scale. As an example, an alignment of 3° inversion of the foot coupled by 2.5° plantarflexion may be duplicated by orienting the two interlocking wedge rings 1402 and 1404 so that the number 13 on the white ring is matched to the number 15 on the red ring. The interlocking teeth in the two rings maintain the alignment while the user tightens a clamping bolt. The tube clamp adaptor 1400 surface includes an index pin 1408 that fits into a slot in the lower surface of the wedge ring 1404. The wedge ring 1404 includes an index mark 1410 on the circumference of the ring that can be the high point in the ring, and which is aligned to the index mark 1410 on the tube clamp adaptor 1400. The surrogate includes a top coupling plate 1406. The top coupling plate 1406 is used to attach the surrogate to the base of the prosthesis socket.

Figure 19:
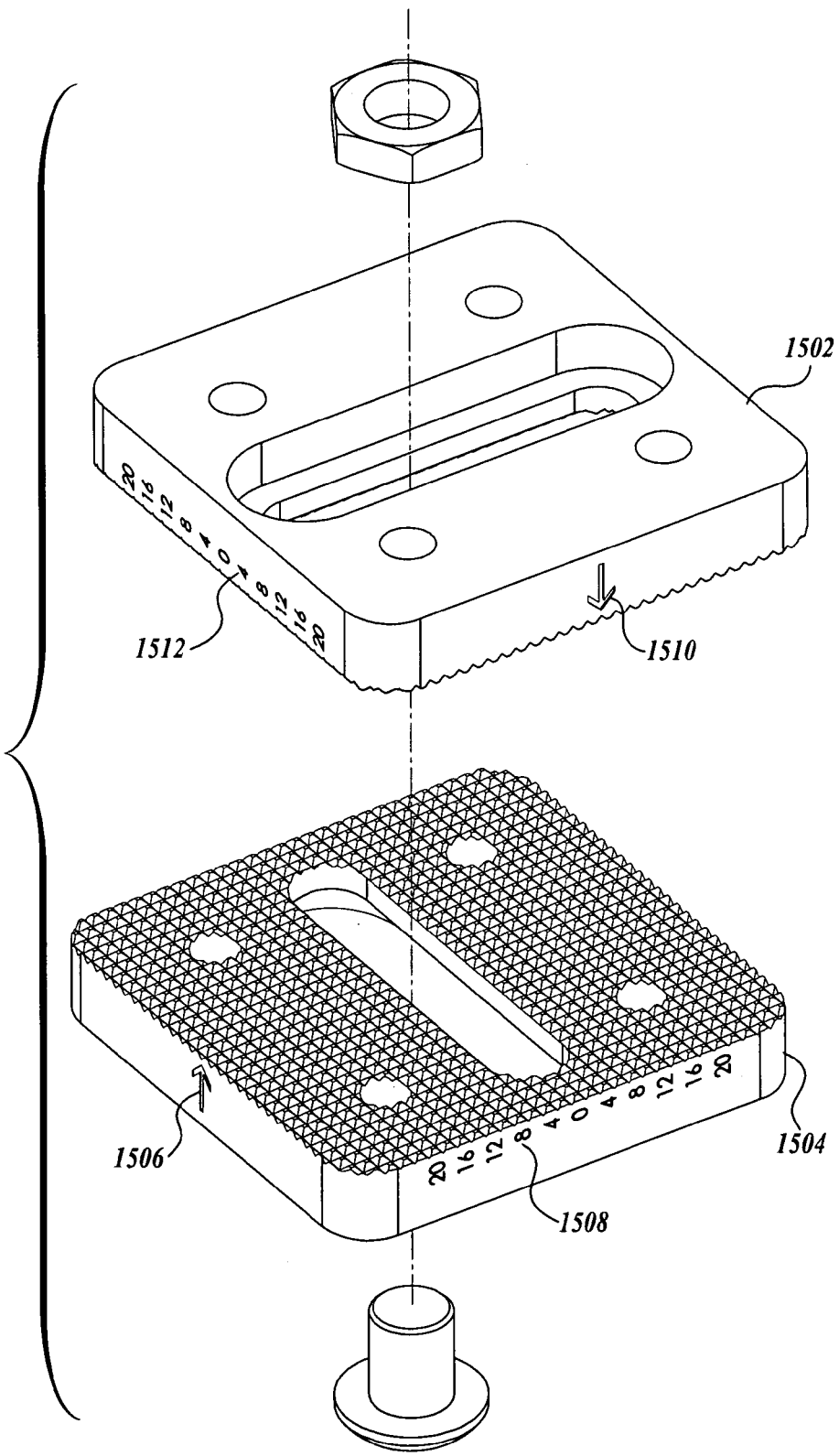
FIG. 19 is a diagrammatical illustration of an exploded view of a surrogate device in accordance with one embodiment of the present disclosure.

Referring to FIG. 19, the surrogate device may also include a horizontal component. The horizontal component would be used in a prosthesis, if horizontal translation was used in alignment. Otherwise, a simple spacer may be added to the surrogate to achieve correct length, i.e., height. The horizontal component of the surrogate includes an upper surrogate deck 1502 and lower surrogate deck 1504. The upper surface of the lower deck 1504 and the lower surface of the upper deck 1502 include locking features. The surfaces having the locking features are placed in contact with each other. The lower deck 1504 includes a slot that has a length greater than the width. The upper deck 1502 includes a slot that has a length greater than the width. In use, the lower deck 1504 and the upper deck 1502 will be placed so that the respective slots are perpendicular to one another. The lower deck 1504 includes an index mark 1506 on one side of the deck 1504 and a graduated scale 1508 on the adjacent side. The upper deck 1502 includes an index mark 1510 on one side of the deck and a graduated scale 1512 on the adjacent side. The scales 1508 and 1512 are dimensionally similar to the scales 121, 126 used on the middle 106 and lower 108 slide decks to be able to directly transfer the alignment to the surrogate. As disclosed herein, the robotic prosthesis alignment device 101 includes a first, second, and third deck in a stacked arrangement. As also disclosed, the upper deck 104 includes an index mark 120, the middle deck 106 includes a graduated scale 121 and an index mark 128, and the lowest deck 108 includes a graduated scale 126. Therefore, with the use of the robotic prosthesis alignment device 101, the translation can be visually read directly from the scales of the middle 106 and lower 108 decks. These readings can then be transferred directly to the upper 1502 and the lower 1504 decks of the surrogate to maintain the same translation that was achieved with the use of the robotic prosthesis alignment device 101. In the horizontal component of the surrogate, the top deck 1502 alignment rotation is located by the four-bolt attachment to the prosthesis socket, while the prosthesis shank is located by marking the shank at the slot of the tube clamp of the actuator, then matching the mark on the shank to the slot in the surrogate tube clamp.

Figure 20:
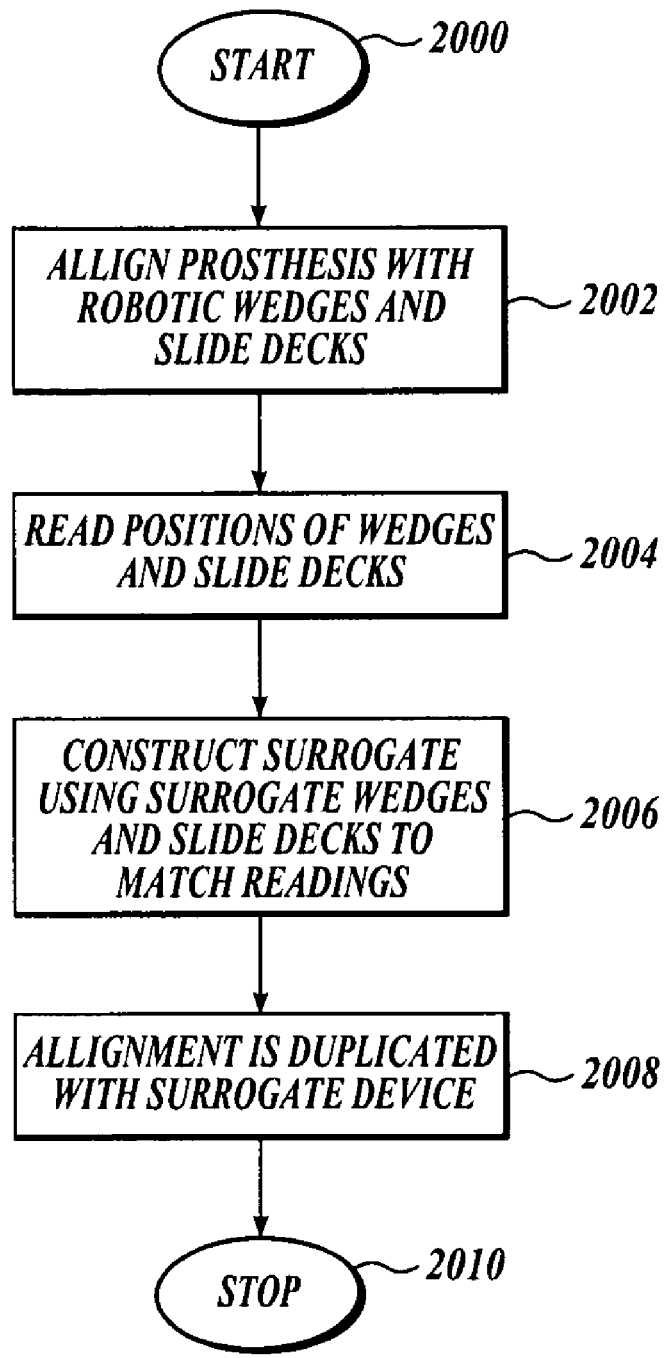
FIG. 20 is a flow diagram of a method of maintaining the alignment of a prosthesis with the use of a surrogate device.

FIG. 20 discloses the method of performing the transfer of the translational and angular alignment from the robotic prosthesis alignment device 101 to the surrogate device. The method starts at start block 2000. From start block 2000, the method enters block 2002. In block 2002, the method uses the robotic prosthesis alignment device to translationally and angularly align the prosthesis in accordance with the method described in association with FIG. 17 using the robotic wedges 140, 142 and the robotic slide decks 104, 106 and 108. When alignment is completed, the method enters block 2004. In block 2004, the positions of the robotic wedges 140, 142 and of the robotic slide decks 104, 106 and 108 are read, either visually or through the use of a computer 300 and software that will provide a position or numerical index denoting the translational and angular positions of the robotic wedges 140, 142 and the robotic slide decks 104, 106, and 108. From block 2004, the method enters block 2006. In block 2006, the method relies on a user or prosthetist to construct a surrogate device using the surrogate wedges 1402 and 1404 and/or the surrogate decks 1502 and 1504. The surrogate is constructed such that the surrogate wedges 1402 and 1404 are placed in a manner to duplicate the angular alignment achieved using the robotic wedges 140, 142 and the surrogate decks 1502 and 1504 are placed in a manner to duplicate the translational alignment using the robotic slide decks 104, 106 and 108. When constructed in such manner, the surrogate device can replace the robotic prosthesis alignment device 101 in the same or different prosthesis. The advantage being that the alignment is not lost and can be retained with the use of a surrogate device.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A combination including a robotic prosthesis alignment device and a surrogate device, comprising:
    a robotic prosthesis alignment device, comprising:
        an angulation assembly comprising a first wedge and a second wedge, each wedge being separately capable of rotation; and
        a first and second driver motor to rotate the first and second wedges, wherein the device provides an indication of the positional relationships of the first and second wedges with respect to each other that represents an angle of tilting; and
    a surrogate device separate from the robotic prosthesis alignment device, comprising:
        a third wedge comprising marks, wherein the marks are determinative of a position on the third wedge; and
        a fourth wedge comprising marks, wherein the marks are determinative of a position on the fourth wedge, wherein the third and fourth wedges are rotationally positionable with respect to each other, wherein when a mark of the third wedge is in alignment with a mark on the fourth wedge in accordance with the indication provided by the robotic prosthetic alignment device, the same angle of tilting results as is in the robotic prosthesis alignment device.

2. The combination of claim 1, wherein the robotic prosthesis alignment device further comprises a translation assembly comprising a first slide deck and a second slide deck that translates in a different direction to the first slide deck and provides displacement of an object attached to the translation assembly along a two dimensional plane.

3. The combination of claim 2, wherein the movement of the first and second slide decks is linear.

4. The combination of claim 2, further comprising a third and fourth driver motor to move the first and second slide decks, wherein the third and fourth driver motors have a revolution counter and the device comprises a processor that correlates a translational position to the number of revolutions.

5. The combination of claim 2, further comprising a sensor for each slide deck that measures the position of the slide deck, and a processor that determines the translational position from the sensor measurement.

6. The combination of claim 1, wherein the angulation assembly provides displacement by tilting an object attached to the angulation assembly.

7. The combination of claim 1, wherein each wedge comprises a circular member that varies in height around the circumference.

8. The combination of claim 1, wherein the first and second driver motors have a revolution counter and the device further comprises a processor that correlates an angular position to the number of revolutions.

9. The combination of claim 1, further comprising a sensor for the first and second wedges that measures the position of the wedge, and a processor that determines the angular position from the sensor measurement.

10. A prosthesis system, comprising:
    a prosthesis socket for receiving an amputated limb;
    a prosthesis shank attached to the prosthesis socket;
    a prosthesis foot attached to the lower end of the prosthesis shank;
    a robotic prosthesis alignment device of claim 1 attached at the joint between the prosthesis socket and the prosthesis shank and/or at the joint between the prosthesis shank and the prosthesis foot; and
    a surrogate device separate from the robotic prosthesis alignment device, comprising:
        a third wedge comprising marks, wherein the marks are determinative of a position on the third wedge; and
        a fourth wedge comprising marks, wherein the marks are determinative of a position on the fourth wedge, wherein the third and fourth wedges are rotationally positionable with respect to each other, wherein when a mark of the third wedge is in alignment with a mark on the fourth wedge in accordance with the indication provided by the robotic prosthetic alignment device, the same angle of tilting results as is in the robotic prosthesis alignment device, and wherein the surrogate device has a geometry configured to replace the robotic prosthesis alignment device in the prosthesis while maintaining the same angle of tilting.

11. The prosthesis system of claim 10, wherein the robotic prosthesis device comprises a translation assembly that displaces the prosthesis socket in relation to the prosthesis foot along a two dimensional plane.

12. The prosthesis system of claim 11, comprising a sensor that measures the linear position of the translation assembly.

13. The prosthesis system of claim 10, wherein the robotic prosthesis alignment device comprises an angulation assembly that tilts the prosthesis socket in relation to the prosthesis foot.

14. The prosthesis system of claim 13, comprising a sensor that measures the angular position of the angulation assembly.

15. The prosthesis system of claim 10, wherein the robotic prosthesis alignment device comprises, a third and fourth driver motor to move the first and second slide decks, wherein the third and fourth driver motors have a revolution counter and the device comprises a processor that correlates a translational position to the number of revolutions.

16. The prosthesis system of claim 10, wherein the first and second driver motors have a revolution counter and the device further comprises a processor that correlates an angular position to the number of revolutions.

17. The prosthesis system of claim 10, further comprising a computer in communication with the robotic prosthesis alignment device, wherein the computer computes a gait cycle profile from an angular position.

18. The prosthesis system of claim 17, further comprising a memory device having stored therein correlations of angular positions to a plurality of gait cycle profiles.

19. The prosthesis of claim 17, further comprising a torque sensor attached to the prosthesis that provides torque measurements to generate a profile of a gait cycle.

20. The prosthesis of claim 17, wherein the computer compares a gait cycle profile generated from angular positions to a gait cycle stored in a database and computes an angular position that approximately matches the gait cycle profile stored in the database.

\* \* \* \* \*